US008513023B2

(12) United States Patent
Gruss et al.

(10) Patent No.: US 8,513,023 B2
(45) Date of Patent: *Aug. 20, 2013

(54) PROGNOSTIC METHOD

(71) Applicant: Norgine BV, Amsterdam Zuid-Oost (NL)

(72) Inventors: Hans-Jürgen Gruss, Middlesex (GB); Ronald Oude Elferink, Amsterdam (NL); Dirk De Waart, Amsterdam (NL); Bruno Stieger, Zurich (CH)

(73) Assignee: Norgine BV, Amsterdam Zuid-Oost (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/660,912

(22) Filed: Oct. 25, 2012

(65) Prior Publication Data

US 2013/0042671 A1 Feb. 21, 2013

Related U.S. Application Data

(63) Continuation of application No. 12/466,292, filed on May 14, 2009, now Pat. No. 8,318,504.

(30) Foreign Application Priority Data

May 15, 2008 (GB) .................... 0808777.7

(51) Int. Cl.
*G01N 33/49* (2006.01)
*G01N 21/64* (2006.01)

(52) U.S. Cl.
USPC ............. 436/129; 436/63; 436/111; 436/119; 436/131; 436/172; 600/317; 600/329

(58) Field of Classification Search
USPC ................... 436/63, 111, 119, 129, 131, 172; 600/312, 317, 329
See application file for complete search history.

(56) References Cited

U.S. PATENT DOCUMENTS

| 4,264,514 A | 4/1981 | Hixson et al. |
| 4,848,349 A | 7/1989 | Sherman et al. |
| 5,154,176 A | 10/1992 | Kanda |
| 6,030,841 A | 2/2000 | Mills |
| 2005/0048464 A1 | 3/2005 | Tian et al. |

FOREIGN PATENT DOCUMENTS

| EP | 0298122 A1 | 1/1989 |
| EP | 1290976 A2 | 3/2003 |
| WO | WO 97/06829 A1 | 2/1997 |
| WO | WO 98/40106 A1 | 9/1998 |

(Continued)

OTHER PUBLICATIONS

Jensen, P I.M. et al., Hepatology 1985, 5, 573-579.

(Continued)

*Primary Examiner* — Arlen Soderquist
(74) *Attorney, Agent, or Firm* — Knobbe Martens Olson & Bear LLP

(57) ABSTRACT

A method of determining the functional activity of the MRP2 and/or MRP3 efflux pathway of a human or animal subject was disclosed. The method comprises (i) determining the level of a bile acid derivative in the blood of said human or animal subject at a predetermined time interval after introducing an amount of the bile acid derivative into the subject, and (ii) using the determination obtained in step (i) to indicate the functional activity of the MRP2 and/or MRP3 efflux pathway of the subject.

9 Claims, 16 Drawing Sheets

(56) References Cited

FOREIGN PATENT DOCUMENTS

| WO | WO 99/07325 A1 | 2/1999 |
|---|---|---|
| WO | WO 00/01297 A1 | 1/2000 |
| WO | WO 01/19238 A1 | 3/2001 |

OTHER PUBLICATIONS

Wilton, J.C. et al., Journal of Cell Biology, 1994, 127, 401-410.
Paulusma C.C et al., Science 1996, 271, 1126-1128.
Swaan, P.W. et al., Advanced Drug Delivery Review 1996, 20, 59-82.
Holzinger, F. et al., Hepatology 1997, 26, 1263-1271.
Bravo, P. et al., Hepatology 1998, 27, 576-583.
Huang, L. et al., Hepatology 2000, 32, 66-72.
Cantz, T. et al., American Journal of Physiology. Gastrointestinal and Liver Physiology 2000. 278, G522-G531.
Bravo, M.G. et al., Hepatology 2000, 32, 1342-1356.
Milkiewicz, P. et al., Journal of Hepatology 2001, 34, 4-10.
Crocenzi, F.A. et al., Hepatology 2001, 34, 329-339.
Schoemaker, M.H. et al., Hepatology 2004, 39, 1563-1573.
Vlaming, M.L.H. et al., Journal of Pharmacology and Experimental Therapeutics 2006. 318, 319-327.
Hopwood et al., "A Novel Method for Quantification of Canalicular transporter inhibition in Primary Rat Hepatocyte Sandwich Cultures," Toxicology, 226(1):66-67 (Sep. 2006).
Akita et al., "Sinusoidal Efflux of Taurocholate Correlates with the Hepatic Expression Level of Mrp3," Biochemical and Biophysical Research Communications 299(5):681-687 (Dec. 2002).
Dirk R. de Waart, et al., "Hepatic Transport Mechanisms of Cholyl-$_L$-Lysyl-Fluorescein," The Journal of Pharmacology and Experimental Therapeutics—334:78-86 (2010).
Akita H, Suzuki H, Ito K, Kinoshita S, Sato N, Takikawa H, et al., Characterization of bile acid transport mediated by multidrug resistance associated protein 2 and bile salt export pump., Biochim Biophys Acta; Mar. 9, 2001; 1511(1); 7-16.
Baringhaus KH, Matter H, Stengelin S, Kramer W, Substrate specificity of the ileal and the hepatic (Na(+)/bile acid cotransporters of the rabbit. II. A reliable 3D QSAR pharmacophore model for the ileal Na(+)/bile acid cotransporter; J Lipid Res, Dec. 1999, vol. 40(12), pp. 2158-2168.
Baxter DJ, Rahman K, Bushell AJ, Mills CO, Elias E, Billington D, Biliary lipid output by isolated perfused rat livers in response to cholyl-lysylfluorescein., Biochim Biophys Acta Jun. 6, 1995, vol. 1256(3), pp. 374-380.
Boyer JL, Ng OC, Ananthanarayanan M, Hofmann AF, Schteingart CD, Hagenbuch B, et al., Expression and characterization of a functional rat liver Na+ bile acid cotransport system in COS-7 cells., Am J Physiol, Mar. 1994, vol. (3 Pt 1), pp. G382-G387.
Evers R. Kool M, van DL, Janssen H, Calafat J, Oomen LC, et al., Drug export activity of the human canalicular multispecific organic anion transporter in polarized kidney MDCK cells expressing cMOAT (MRP2) cDNA., J. Clin Invest, Apr. 1, 1998, vol. 101(7), pp. 1310-1319.
Gerk, et al. , J Pharmacol Exp Ther, Aug. 2002, vol. 302(2), pp. 407-415.
Geyer J, Wilke T, Petzinger E, The solute carrier family SLC10: more than a family of bile acid transporters regarding function and phylogenetic relationships, Naunyn Schmiedebergs Arch Pharmacol, Mar. 2006, vol. 372(6), pp. 413-431.
Hagenbuch B, Dawon P, The sodium bile salt cotransport family SLC10, Pflugers Arch, 2004, vol. 447(5), pp. 566-570.
Hagenbuch B, Meier PJ, Organic anion transporting polypeptides of the OATP/SLC21 family; phylogenetic classification as OATP/SLCO superfamily, new nomenclature and molecular/functional properties., Pflugers Arch, Feb. 2004, vol. 447(5), pp. 653-665.
Jedlitschky, et al., Expert Opin Drug Metab Toxicol, Jun. 2006, vol. 2(3), pp. 351-366.
Keitel V, Burdelski M, Warskulat U, Kuhlkamp T, Keppler D, Haussinger D, et al., Expression and localization of hepatobiliary transport proteins in progressive familial intrahepatic cholestasis, Hepatology, May 2005, vol. 41(5), pp. 1160-1172.
Kojima H, Nies AT, Konig J, Hagmann W, Spring H, Uemura M, et al., Changes in the expression and localization of hepatocellular transporters and radixin in primary biliary cirrhosis, J Hepatol, Nov. 2003, vol. 39(5), pp. 693-702.
Kullak-Ublick GA, Baretton GB, Oswald M, Renner EL, Paumgartner G, Beuers U, Expression of the hepatocyte canalicular multidrug resistance proteion (MRP2) in primary biliary cirrhosis, Hepatol Res, May 2002, vol. 23(1), pp. 78-82.
Kullak-Ublick GA, Glasa J, Boker C, Oswald M, Grutzner U, Hagenbuch B, et al., Chlorambucil-taurocholate is transported by bile acid carriers expressed in human hepatocellular carcinomas., Gastroenterology, Oct. 1997, vol. 113(4), pp. 1295-1305.
Lee G, Piquette-Miller M., Influence of IL-6 on MDR and MRP-mediated multidrug resistance in human hepatoma cells., Can J. Physiol Pharmacol, Oct. 2001, vol. 79(10), pp. 876-884.
Maglova LM, Jackson AM, Meng XJ, Carruth MW, Schteingart CD, Ton-Nu HT, et al., Transport characteristics of three fluorescent conjudgated bile acid analogs in isolated rat hepatocytes and couplets., Hepatology, Aug. 1995, vol. 22(2), pp. 637-647.
Meier PJ, Stieger B, Bile salt transporters. Annu Rev Physiol, 2002, vol. 64, pp. 635-661.
Milkiewicz P, Saksena S, Cardenas T, Mills CO, Elias E, Plasma elimination of cholyllysyl-fluorescein (CLF): a pilot study in patients with liver cirrhosis. Liver, Jul. 2000, vol. 20(4), pp. 330-334.
Mills CO, Milkiewicz P, Muller M, Roma MG, Havinga R, Coleman R, et al., Different pathways of canalicular secretion of sulfated and non-sulfated fluorescent bile acids: a study in isolated hepatocyte couplets and TR-rats., J Hepatol, Oct. 1999, vol. 31(4), pp. 678-884.
Mills CO, Rahman K, Coleman R, Elias E, Cholyl-lysylfluorescein; synthesis, biliary excretion in vivo and during single-pass perfusion of isolated perfused rat liver., Biochim Biophys Acta, Dec. 6, 1991, vol. 1115(2), pp. 151-156.
Milkiewicz et al., Journal of Hepatology, 1997, vol. 27, Issue 1106-1109.
Nies, et al, Pflugers Arch, 2007, vol. 453, pp. 643-659.
Paumgartner G, Medical treatment of cholestatic liver diseases; From pathobiology to pharmacological targets. World J Gastroenterol, Jul. 28, 2006, vol. 28, pp. 4445-4451.
Sakka SG, Assessing liver function. Curr Opin Crit Care, Apr. 2007, vol. 13(2), pp. 207-214.
Stieger B, Meier Y, Meier PJ, The bile salt export pump. Pflugers Arch, Feb. 2007, vol. 5, pp. 611-620.
Wong MH, Oelkers P, Dawson PA, Identification of a mutation in the ileal sodium-dependent bile acid transporter gene that abolishes transport activity, J Biol Chem, Nov. 10, 1995, vol. 270(45), pp. 27228-27234.
Zollner G, Fickert P, Silbert D, Fuchsbicher A, Marschall HU, Zatloukal K, et al., Adaptive changes in hepatobiliary transporter expression in primary biliary cirrhosis. J Hepatol, Jun. 2003, vol. 38(6), pp. 717-727.
Zollner G, Wagner M, Fickert P, Silbert D, Gumhold J, Zatloukal K, et al., Expression of bile acid synthesis and detoxification enzymes and the alternative bile acid efflux pump MRP4 in patients with primary biliary cirrhosis, Liver Int, Sep. 2007, vol. 27(7), pp. 920-929.
Yamaguchi H. et al, Transport of fluorescent chenodeoxycholic acid via the human organic anion transporters OATP1B1 and OATP1B3, J. Lipid Res. 2006, vol. 47, pp. 1196-1202.

PROGNOSTIC METHOD

CROSS-REFERENCE TO RELATED APPLICATIONS

This application is a continuation of U.S. patent application Ser. No. 12/466,292, filed May 14, 2009, now U.S. Pat. No. 8,318,504, which claims the benefit and priority to UK Patent Application No. 0808777.7 filed May 15, 2008. The disclosures of all of the foregoing applications are hereby incorporated by reference in their entireties.

BACKGROUND OF THE INVENTION

1. Field of the Invention

A new method relates to determining the functional activity of the MRP2 and/or MRP3 efflux pathway of a human or animal subject, and to the use of a bile acid derivative in such a method.

2. Background of the Invention

MRP2/Mrp2 (ABCC2/Abcc2), also known as Multidrug Resistance Protein 2, is a member of the ABCC subfamily of the ATP-Binding Cassette Transporter superfamily. An overview of the ATP-Binding Cassette transporter family is given in 'The Human ATP-Binding Cassette (ABC) Transporter Superfamily' by Michael Dean of the National Cancer Institute at Frederick, Md., published by the US National Center for Biotechnology Information. MRP2 is expressed on the apical domain of hepatocytes, enterocytes of the proximal small intestine, and proximal renal tubular cells, as well as in the brain and the placenta.

MRP2 is important clinically as it modulates the pharmacokinetics of many drugs, and its expression and activity are also altered by a range of drugs and diseases. For example, expression of MRP2 is altered in patients with liver diseases such as primary biliary cirrhosis, cholestasis (e.g. drug-induced cholestasis), fatty liver disease, alcoholic liver disease, primary sclerosing cholangitis, or viral hepatitis. In the kidney, MRP2 functions in renal elimination of substrates from the blood into urine. In the liver, MRP2 is the major exporter of organic anions from the liver into the bile. MRP2 can transport sulphated and glucuronidated bile salts as well as other organic anions and/or their conjugates with glucuronate, glutathione and sulphate [Gerk et al. J Pharmacol Exp Ther 2002 August; 302(2):407-415]. In addition to transport of conjugates, MRP2 transports a range of molecules including cancer chemotherapeutics, uricosurics, antibiotics, leukotrienes, glutathione, toxins and heavy metals. MRP2 also plays an important role in the elimination of bilirubin glucuronosides from hepatocytes into bile. The MRP2 gene is mutated in patients with Dubin-Johnson syndrome, a human disorder of the organic ion transport. The absence of functional MRP2 from the canalicular membrane causes conjugated hyperbilirubinemia, as observed in the hereditary disorder Dubin-Johnson syndrome.

Loss of MRP2 function is often well tolerated and compensated by the upregulation of other membrane transporters, particularly Multidrug Resistance Protein 3 (MRP3, also known as ABCC3) in the basolateral member of hepatocytes [Nies et al. Pflugers Arch (2007) 453:643-659]. Like MRP2, MRP3 is a member of the ABCC subfamily of the ATP-binding cassette transporter superfamily. MRP3 is present in the intestine, kidney and the liver.

Knowledge of the state of the MRP2/3 activity of a subject therefore could be used to indicate a wide range of possible conditions.

It would therefore be advantageous to provide a method of determining the functional activity of the MRP2 and/or MRP3 efflux pathway of a human or animal subject.

We have unexpectedly found that MRP2 is the most prominent transporter responsible for biliary excretion of cholyl lysyl fluorescein (CLF), which is also known as fluorescein lisicol, and that MRP3 is responsible for basolateral excretion of CLF. Accordingly, CLF and other bile acids having a similar metabolic/elimination pathway can be used in determining the functional activity of MRP2/3 efflux pathway.

Some aspect of the present invention is particularly surprising in view of the disclosure of Mills et al. in Biochim Biophys Acta 1991 Dec. 6; 1115(2):151-156. They showed that, in rats, the biliary excretion rate of CLF after jugular vein injection has similar kinetics to that of glycocholate, the transport of which is known to be mediated by ABCB11. ABCB11 is a member of the ABCB subfamily of the ATP-binding cassette (ABC) transporter superfamily.

Other evidence that led to the belief that CLF is transported via ABCB11 was provided by Baxter et al. [Biochim Biophys Acta 1995 Jun. 6; 1256(3):374-380]. Baxter et al. administered glycocholate and CLF to isolated perfused rat livers under recycling conditions, and observed that CLF was capable of increasing phospholipids and cholesterol output in a similar way to that which was found for glycocholate. It was shown in the same study that rat liver has a much greater capacity to transfer glycocholate (GC) from perfusate to bile than CLF and concomitantly, the increase in phospholipid and cholesterol output was less with CLF in comparison with GC.

In a later study [Mills et al. in J Hepato 11999 October; 31(4):678-684], Mills et al. investigated ABCC2/Abcc2 as a possible transporter for CLF. But they concluded from a study with normal and TR⁻ (Abcc2 deficient) Wistar rats that Abcc2 was not involved in the biliary excretion of CLF, based on the observation of similar biliary excretion in both strains.

In summary, prior to the present investigations, the totality of the prior art on the subject concluded unanimously that CLF was transported from the liver into bile by the ABCB11/Abcb11 pathway, rather than the ABCC2/Abcc2 pathway, and therefore would not have been considered as an agent for use in a method for the determination of MRP2/3 activity.

SUMMARY OF THE INVENTION AND DETAILED DESCRIPTION

Accordingly, there is provided a method of determining the functional activity of the MRP2 and/or MRP3 efflux pathway of a human or animal subject, said method comprising:

1. A method of determining the functional activity of the MRP2 and/or MRP3 efflux pathway of a human or animal subject, said method comprising:—

(i) determining the level of a bile acid derivative in the blood of said human or animal subject at a predetermined time interval after introducing an amount of the bile acid derivative into the subject; and (ii) using the determination obtained in step (i) to indicate the functional activity of the MRP2 and/or MRP3 efflux pathway of the subject.

According to a further aspect there is provided a method of performing a prognosis or diagnosis on a human or animal subject, said method comprising:

determining the level of a bile acid derivative in the blood of said human or animal subject at a predetermined time interval after introducing an amount of the bile acid derivative into the subject, performing a prognosis or diagnosis based on determination obtained, wherein the determination is used to indicate the functional activity of the MRP2 and/or MRP3 efflux pathway of the subject.

The term "determining" in this context has a broad meaning. It includes both quantitative analysis to quantify the level or amount of the bile acid derivative in the sample and qualitative analysis to detect whether or not the bile acid is present and, if appropriate, the degree to which it is present. Thus it is not essential for this method that a numerical value for the level of bile acid derivative in the blood is obtained. For example, ascertaining that the level of the bile acid derivative in the blood is within a certain range can be used to assess functional activity of the MRP2 and/or MRP3 pathway. By analogy, the words "determine" and "determination" are to be given a similar meaning.

The determination of the level of the bile acid can be carried out as described in European patent specification no. EP1,003,458 (the entire text of which is hereby imported by reference and which is intended to form an integral part of this disclosure). That specification describes the use of coloured or fluorescent bile acid derivatives in human subjects to determine the liver function of the subject. One example of such a bile acid derivative given in EP 1,003,458 is the fluorescent fluorescein derivative, cholyl lysyl fluorescein (CLF). EP 1,003,458 discloses the use of CLF as a potential liver function test.

The purpose of using a bile acid derivative compound, such as CLF, in a liver function test was to provide a compound which would be transported from hepatocytes into bile in the same way as natural bile acids. Bile acids are taken up into liver cells by at least two transport systems: a Na+ dependent system, involving Na+/taurocholate cotransporter polypeptide (known as NTCP) and a Na+ independent system, involving transporters in the organic anion transporter family (known as the OATP family). Bile acids are excreted into the bile ducts by the bile salt export pump, also known as BSEP or ABCB11, which expresses on the bile duct side of liver cells. As described above, prior to the present invention, it was believed that CLF is excreted into bile via ABCB11.

Instead, we have found that the above method can be used to indicate the functional activity of the MRP2 and/or MRP3 efflux pathway of a subject. MRP2/MRP3 expression and activity are altered by a wide range of drugs and disease states, therefore knowledge of the functional activity of the MRP2 and/or MRP3 elimination pathway of the subject can be used to indicate a wide range of conditions including those mentioned herein. This method is therefore useful in the diagnosis or prognosis of a range of conditions selected from those wherein MRP2 and/or MRP3 expression is modified, such as up-regulated or down-regulated, or wherein the MRP2 and/or MRP3 gene is mutated. In some aspects, the method of the present invention is used to diagnose or prognose a condition or disease specified herein.

The terms "functional activity of the MRP2 and/or MRP3 efflux pathway" or "functional activity of the MRP2 and/or MRP3 elimination pathway" as used herein refers to the transport activity of the MRP2 transporter protein and/or the MRP3 transporter protein in transporting substrates across cellular membranes.

The determination of the level of a bile acid derivative in the blood can be processed or analyzed in a number of ways. The level of the bile acid derivative in the blood may be compared with at least one standard measurement. Similarly results taken at different predetermined time intervals may be compared with such standard measurements.

However, it is not necessary to make a comparison with a standard. It is possible to use the determination obtained to give a direct indication of the functional activity of the MRP2 and/or MRP3 elimination pathway of a subject, without the need for any comparison with results from a healthy subject or from a subject with known MRP2/3 function.

In some aspects, the method comprises a further step of using the determination of the level of the bile acid derivative to arrive at a numerical value, wherein the numerical value indicates the functional activity of the MRP2 and/or MRP3 efflux pathway of the subject. A single numerical value indicating the functional activity of the MRP2 and/or MRP3 efflux pathway of the subject advantageously provides a useful means for physicians to assess functions of a patient that are affected by MRP2/3 activity, such as liver function, kidney function, or intestinal function. Said numerical value may be obtained by using the determination of the level of bile acid derivative to give a direct measure of the functional activity of the MRP2 and/or MRP3 efflux pathway of the subject.

In some aspects, the determination obtained is compared with at least one standard to indicate the functional activity of the MRP2 and/or MRP3 efflux pathway of the subject.

In some aspects, the level of the bile acid derivative in the blood of the subject is determined at two or more predetermined time intervals after introducing an amount of the bile acid derivative into the subject. By taking a series of blood samples over time, a plasma elimination curve may be constructed and compared with plasma elimination curves obtained from subjects having known MRP2/3 activity. Two or more determinations of level of the bile acid derivative in the blood of the subject taken at different time intervals may be used to obtain said numerical value indicating the functional activity of the MRP2 and/or MRP3 elimination pathway of the subject.

For example, when the level of the bile acid derivative in the blood of the subject is determined at two or more predetermined time intervals, the determination obtained at a first time interval after administration and the determination obtained at a second time interval after administration can be expressed as a ratio or as a percentage. Thus a ratio of the determination after 30 minutes or after 60 minutes may be expressed as a ratio of the determination after 10 minutes. This ratio provides a numerical value, generally less than unity, which gives an indication of the functional activity of the MRP2 and/or MRP3 pathway of the subject.

Alternatively, the determination at the later time interval, e.g., 30, 60 or 90 minutes, may be expressed as a percentage of the determination at the earlier time interval e.g., 10 minutes, following administration of the bile acid derivative. This percentage figure likewise gives an indication of the functional activity of the MRP2 and/or MRP3 pathway of the subject.

Alternatively, a numerical value indicating the functional activity of the MRP2/3 pathway of a subject may be obtained by determining the slope of a log-linear plasma elimination curve derived from the determinations obtained. Alternatively, a numerical value may be obtained by determining the area under a plasma elimination curve derived from the results. Furthermore, the difference between the slopes of a log-linear plot derived from a test plasma elimination curve and a log-linear plot derived from a standard elimination curve can be calculated to provide said numerical value indicating the functional activity of the MRP2 and/or MRP3 pathway. Similarly, the difference between the areas under the plasma elimination curve derived from test results and a standard elimination curve can be calculated to provide said numerical value.

The term "standard" in this context has a broad meaning. It is intended to encompass any single measurement or series (two or more) of measurements taken from a human or animal subject. This includes measurements taken from healthy subjects, subjects with known MRP2/3 function, and can include a measurement or measurements taken from the subject whose MRP2/3 function is being investigated. That is to say, when one is concerned with the progression or staging of a disease one may compare measurements taken over time with the subject him(her)self acting as a control.

In some aspects, the bile acid derivative comprises a detection marker such as a colour or a fluorescence, to aid in detecting the bile acid derivative In some aspects, the method further comprises the step of providing at least one sample of blood which has passed through the liver of the subject and which sample has been collected at a predetermined time interval after administering the bile acid derivative to the subject, wherein the blood sample(s) are processed to obtain blood plasma or blood serum. Therefore, an in vitro method for determining the functional activity of the MRP2 and/or MRP3 efflux pathway of a subject may be provided.

In some aspects, the blood sample(s) are processed by centrifugation. The blood proteins are separated from the blood plasma/blood serum.

In some aspects, the bile acid derivative is administered to the subject intravenously.

In some aspects, the bile acid derivative comprises (a) a steroid moiety having (i) at least one substituent selected from the group consisting of a 3-hydroxyl substituent, a 7-hydroxyl substituent and a 12-hydroxyl substituent, and (ii) a carboxyl group attached by means of an amide linkage to a side chain of the steroid moiety; and (b) an active moiety which is to be targeted to the liver, said active moiety being attached to an α-carbon atom relative to the carboxyl group.

In further aspects, the bile acid derivative has the general formula (I):—

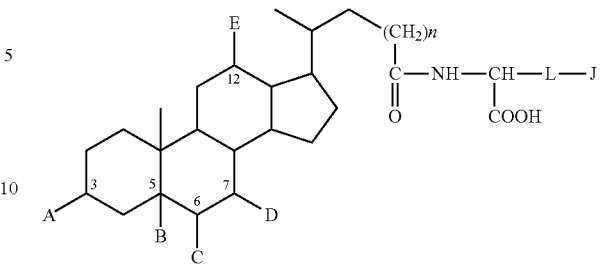

(I)

wherein A is selected from the group consisting of α-OH and β-OH; B is selected from the group consisting of α-H and β-H; C is selected from the group consisting of —H, α-OH and β-OH; or B and C together form a double bond; D is selected from the group consisting of —H, α-OH and β-OH; E is selected from the group consisting of —H, α-OH and β-OH; L is a linking moiety; J is a coloured or fluorescent moiety; and n is 0 or 1.

In the formula above the linking moiety, L, is in some aspects N-terminated at its end attached to the coloured or fluorescent moiety, J, and is preferably —(CH$_2$)$_n$NH, where n is 3 or 4, —(CH$_2$)$_4$NH—(CH$_2$)$_3$NHC(=NH)NH—, or —(CH$_2$)$_2$—CH(OH)CH$_2$NH—.

Alternatively, the moiety —NH—CH(COOH)-L- may be derived from S-adenosylhomocysteine, S-adenosylmethionine, S-amino-imadazole-4-carboxamide, asparagine, cadaverine, cystamine, citrulline, diaminopimelic acid, 2,4-diaminobutyric acid, cysteamine, glutamine, 3-hydroxykynurenine, kynurenine, putrescine or negamycin. Alternatively, acidic amino acids can be used instead of the above where active moiety J has one amino group and/or is hydrophobic.

In some aspects of the formula above, J is or includes a fluorescein, rhodamine or other fluorescing moiety.

The steroid moiety of the bile acid derivative may be based on an acid selected from the group consisting of cholic acid, chenodeoxycholic acid, deoxycholic acid, hyodeoxycholic acid, hyocholic acid, α-, α- or ω-muricholic acid, nor-bile acids, lithocholic acid, 3 β-hydroxycholenoic acid, ursodeoxycholic acid and allocholic acid (5α-cholan-24-oic-acid).

The bile acid derivative may be a cholyl-lysyl-fluorescein (CLF) having the formula:—

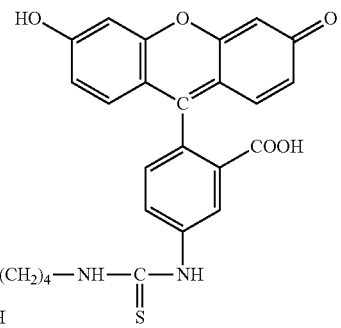
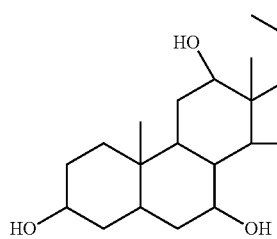

or salts thereof. In some aspects, the bile acid derivative is a trisodium salt. The bile acid derivative may be cholyl-L-lysyl-fluorescein, also known as fluorescein lisicol. The bile acid derivative may be fluorescein lisicol trisodium salt.

According to a further aspect there is provided use of MRP2 and/or MRP3 functional activity obtained from the above method for determining the liver function of a human or animal subject.

According to a further aspect there is provided a method of determining the liver function of a human or animal subject, said method comprising the steps of:—
(i) determining the level of a bile acid derivative in the blood of said human or animal subject at a predetermined time interval after introducing an amount of the bile acid derivative into the subject,
(ii) using the determination obtained in step (i) to indicate the functional activity of the MRP2 and/or MRP3 efflux pathway of the subject, and
(iii) using the determination of the MRP2 and/or MRP3 functional activity obtained in step (ii) to indicate the liver function of said human or animal subject.

According to a further aspect there is provided use of a bile acid derivative for determining the functional activity of the MRP2 and/or MRP3 efflux pathway of a human or animal subject.

According to a further aspect there is provided use of a bile acid derivative in the diagnosis or prognosis of Dubin-Johnson syndrome, cirrhosis of the liver, cholestasis, fatty liver disease, alcoholic liver disease, primary sclerosing cholangitis, or viral hepatitis.

According to a further aspect there is provided use of a bile acid derivative in the manufacture of a diagnostic or prognostic agent for use in the diagnosis or prognosis of Dubin-Johnson syndrome, cirrhosis of the liver, cholestasis, fatty liver disease, alcoholic liver disease, primary sclerosing cholangitis, or viral hepatitis.

According to a further aspect there is provided use of a bile acid derivative in determining the state of the bilirubin clearance pathway or conjugated bilirubin clearance pathway of a human or animal subject.

According to a further aspect there is provided use of a bile acid derivative in the manufacture of a diagnostic or prognostic agent for determining the state of the bilirubin clearance pathway or conjugated bilirubin clearance pathway of a human or animal subject.

According to a further aspect there is provided use of a bile acid derivative for determining the kidney function, biliary function, intestinal function, or liver function of a human or animal subject.

According to a further aspect there is provided use of a bile acid derivative in the manufacture of a diagnostic or prognostic agent for determining the kidney function, biliary function, intestinal function, or liver function of a human or animal subject.

Preferably said bile acid derivative comprises (a) a steroid moiety having (i) at least one substituent selected from the group consisting of a 3-hydroxyl substituent, a 7-hydroxyl substituent and a 12-hydroxyl substituent, and (ii) a carboxyl group attached by means of an amide linkage to a side chain of the steroid moiety; and (b) an active moiety which is to be targeted to the liver, said active moiety being attached to an α-carbon atom relative to the carboxyl group.

Preferably said bile acid derivative is a compound of formula (I):

(I)

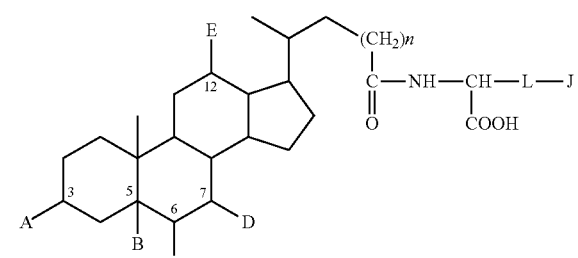

wherein A is selected from the group consisting of α-OH and β-OH; B is selected from the group consisting of α-H and β-H; C is selected from the group consisting of —H, α-OH and β-OH; or B and C together form a double bond; D is selected from the group consisting of —H, α-OH and β-OH; E is selected from the group consisting of —H, α-OH and β-OH; L is a linking moiety; J is a coloured or fluorescent moiety; and n is 0 or 1.

In some aspects, J is or includes a fuorescein, rhodamine or other fluorescing moiety.

In some aspects, the linking moiety is N-terminated at its end attached to active moiety J, and L is selected from the group consisting of: —(CH$_2$)$_n$NH, where n is 3 or 4,
—(CH$_2$)$_4$NH—(CH$_2$)$_3$NHC(=NH)NH—, and
—(CH$_2$)$_2$—CH(OH)CH$_2$NH—.

In some aspects, the moiety —NH—CH(COOH)-L- in the general formula (I) is derived from a compound selected from the group consisting of S-adenosylhomocysteine, S-adenosylmethiodine, S-aminoimadazole-4-carboxamide, asparagine, cadaverine, cystamine, citrulline, diaminopimelic acid, 2,4-diaminobutyric acid, cysteamine, glutamine, 3-hydroxykynurenine, kynurenine, putrescine and negamycin.

In some aspects, the steroid moiety of the bile acid derivative is based on an acid selected from the group consisting of cholic acid, chenodeoxycholic acid, deoxycholic acid, hyodeoxycholic acid, hyocholic acid, α-, β- or ω-muricholic acid, nor-bile acids, lithocholic acid, 3 β-hydroxycholenoic acid, ursodeoxycholic acid and allocholic acid (5α-cholan-24-oic-acid).

Preferably the bile acid derivative is a cholyl-lysyl-fluorescein (CLF) having the formula:—

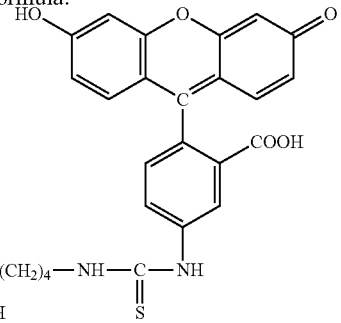

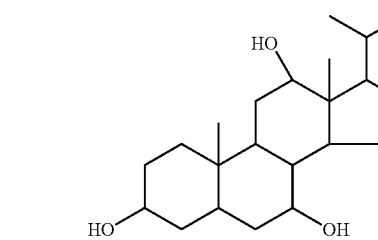

or salts thereof. Preferably the bile acid derivative is a trisodium salt. Preferably the bile acid derivative is fluorescein lisicol trisodium salt.

The Applicant has unexpectedly found that, contrary to the teaching of the prior art, MRP2 and MRP3 transport compounds of general formula (I). A compound of said formula can therefore be used for determining the functional activity of the MRP2 and/or MRP3 pathway of a human or animal subject.

The compounds of formula (I) may be used in the diagnosis or prognosis of Dubin-Johnson syndrome or in the manufacture of a diagnostic or prognostic agent for use in the diagnosis or prognosis of Dubin-Johnson syndrome. Dubin-Johnson syndrome is linked to mutations in the MRP2 gene. Accordingly determination of the activity MRP2 and/or MRP3 pathway of a subject can provide information for use in diagnosis or prognosis relating to Dubin-Johnson syndrome.

The compounds of formula (I) may also be used in determining the kidney function, biliary function, intestinal function, or liver function of a human or animal subject, or used in the manufacture of a diagnostic or prognostic agent for determining the kidney function, biliary function, intestinal function, or liver function of a human or animal subject. MRP2 is expressed in the kidney, intestine and liver, therefore determination of the activity MRP2 and/or MRP3 pathway of a subject can provide information for use in determining kidney function, biliary function, intestinal function, or liver function of a subject.

The compounds of formula (I) may also be used in diagnosis or prognosis of cirrhosis of the liver, cholestasis, fatty liver disease, alcoholic liver disease, primary sclerosing cholangitis, or viral hepatitis, or in the manufacture of a diagnostic or prognostic agent for use in the diagnosis or prognosis of cirrhosis of the liver, cholestasis, fatty liver disease, alcoholic liver disease, primary sclerosing cholangitis, or viral hepatitis.

The compounds of formula (I) may also be used in determining the state of the bilirubin clearance pathway or conjugated bilirubin clearance pathway of a human or animal subject, or in the manufacture of a diagnostic or prognostic agent for determining the state of the bilirubin clearance pathway or conjugated bilirubin clearance pathway of a human or animal subject.

Bilirubin is a breakdown product of heme catabolism. In the liver, bilirubin is conjugated with glucuronic acid and is excreted in bile. Bilirubin and conjugates of bilirubin, including as bilirubin glucuronides such as glucuronosyl-bilirubin, are transported via MRP2 [Jedlitschky et al., Expert Opin Drug Metab Toxicol 2006 Jun. 2(3):351-66]. Increased levels of conjugated bilirubin in plasma indicate a possible disorder in biliary transport of conjugated bilirubin, hence serum bilirubin levels are useful in predicting mortality of liver transplantation candidates.

Bilirubin and bilirubin conjugates are transported via the MRP2 efflux pathway, therefore determinations of the functional activity of the MRP2 and/or MRP3 efflux pathway can be used to determine clearance activity of bilirubin or conjugated bilirubin. Determination of bilirubin and conjugated bilirubin clearance can give an indication of the state of the bilirubin efflux pathway. By determining the state of the bilirubin clearance pathway or conjugated bilirubin clearance pathway of a subject, this can indicate disorders in bilirubin or conjugated bilirubin transport.

The terms "bilirubin clearance pathway" and "conjugated bilirubin clearance pathway" as used herein refer to the transport of bilirubin/conjugated bilirubin across cellular membranes.

According to a further aspect, there is provided a computer program for determining the functional activity of the MRP2 and/or MRP3 elimination pathway of a human or animal subject by using a determination of the level of a bile acid derivative in the blood of a human or animal subject at a predetermined time interval after introducing an amount of the bile acid derivative into the subject to arrive at a numerical value, wherein the numerical value indicates the functional activity of the MRP2 and/or MRP3 elimination pathway of the subject.

According to a further aspect, there is provided a method of determining the functional activity of the OATP1B3 uptake pathway of a human or animal subject, said method comprising:

(i) determining the level of a bile acid derivative in the blood of said human or animal subject at a predetermined time interval after introducing an amount of the bile acid derivative into the subject; and (ii) using the determination obtained in step (i) to indicate the functional activity of the OATP1B3 uptake pathway of the subject.

Previous studies showed partial sodium-dependent uptake of some, but not all, fluorescent bile salts into rat hepatocytes [Maglova LM et al., Hepatology 1995 August; 22(2):637-647]. In addition, uptake of cholyl-glycyl-fluorescein into CHO cells expressing rat Ntcp, but not wild type cells, has been demonstrated [Boyer J L et al., Am J Physiol 1994 March; 266(3 Pt 1):G382-G387]. It could therefore be expected that CLF may be taken up into hepatocytes via NTCP. Instead, we have found that CLF is taken up into hepatocytes via OATP1B3, and we have found that the above method can be used to indicate the functional activity of the OATP1B3 uptake pathway of a subject.

Other aspects relate to a kit containing one or more components used in the methods above, such as bile acid derivatives and optionally a standard.

The preferred features of this aspect of the invention are as described above in relation to the previously described aspects of the invention.

BRIEF DESCRIPTION OF THE DRAWINGS

The invention will now be described by way of example with reference to the drawings, in which:

In FIG. 1A, the fluorescent parts of the micrograph appear dark and the non-fluorescent parts appear white. NTCP is a protein that mediates uptake of bile acids into liver cells. NTCP was visualized as described in the material and methods section below.

FIG. 2A shows fluorescence pictures after incubation of CHO transporter cells with 1 μmol/L CLF over 5 minutes. Fluorescent pictures (right panels) are complemented with phase contrast pictures (left panels). In the fluorescence pictures (right panels), the fluorescent parts appear dark and the non-fluorescent parts appear white.

FIG. 2B is a graph showing transport of CLF mediated by NTCP in the presence (black bars) and absence of sodium (white bars) for 1 and 5 minutes.

FIG. 2C is a graph showing transport of CLF for CHO cells (wild type and cells transfected with OATP1B1, OATP1B3 and OATP2B1). Cells were incubated with μmol/L CLF during 1 (white bar) or 5 minutes (black bars).

FIG. 2D relates to kinetics of OATP1B3 mediated CLF transport and shows a graph of CLF transport against CLF concentration. Cells were incubated with increasing concentrations of CLF for 45 seconds. Shown are uptake rates corrected for 0 seconds binding.

FIG. 3A shows the results for CHO cells expressing NTCP with 2.5 μmol/L TC.

FIG. 3B shows the results for CHO cells expressing OATP1B1 with 1 μmol/L estrone-3-sulfate.

FIG. 3C shows the results for CHO cells expressing OATP1B3 with 10 μmol/L TC.

FIG. 3D shows the results for CHO cells expressing OATP2B1 with 1 μmol/L estrone-3-sulfate.

EXAMPLE 1

Figure 1A:
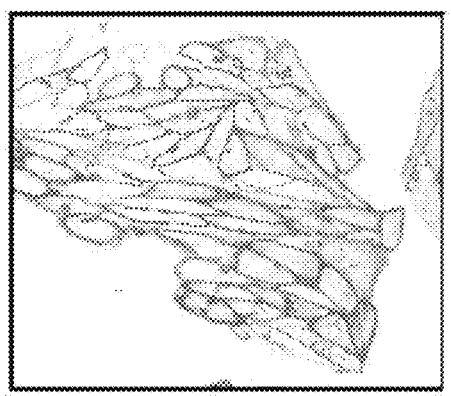
FIG. 1A is an immunofluorescence micrograph showing expression of $Na^+$/taurocholate cotransporter polypeptide (NTCP) in stably transfected cells.

Demonstration that the Bile Acid Derivative CLF is a Substrate for MRP2

(i) Materials

Cholyl lysyl fluorescein (CLF) was obtained from Norgine, Harefield, United Kingdom. [$^3$H]GSH (52 Ci/mmol) and [$^3$H]TC (1.19 Ci/mmol) were obtained from Perkin Elmer Life and Analytical Sciences (Boston, Mass., USA). [$^3$H]DNP-SG synthesis was performed as described by de Waart DR et al. [Liver Int 2006 April; 26(3):362-368]. [$^3$H]E$_2$17βG (40.5 Ci/mmol) was purchased from NEN Life Science Products (Boston, Mass., USA). Cellulose acetate membrane filters were bought from Schleicher and Schuell (Dassel, Germany). Sucrose was obtained from Brunschwig Chemie (Amsterdam, The Netherlands). Creatine phosphate was purchased from Boehringer Mannheim (Almere, The Netherlands). Creatine kinase was bought from Roche Diagnostics (Mannheim, Germany). Methanol (HPLC grade) was obtained from Baker (Deventer, The Netherlands). Triton X-100 was bought from Merck (Darmstadt, Germany). All other chemicals and reagents were purchased from Sigma-Alldrich (Zwijndrecht, The Netherlands).

(a) Animals

Abcc2$^{-/-}$ mice (against a Friend virus B-type (FVB) background) were bred at the National Cancer Institute (Amsterdam, The Netherlands). Production and characterization of the Abcc2$^{-/-}$ mice was as described by Vlaming et al. [J Pharmacol Exp Ther 2006 July; 318(1):319-327]. Wild type and Abcc3$^{-/-}$ mice (against an FVB background) were bred at the animal institute of the Academic Medical Center. Production and characterization of the Abcc3$^{-/-}$ mice was as described by Zelcer et al. [J Hepatol 2006 April; 44(4):768-775].

Generation of CHO Cells Stably Expressing NTCP and Cell Lines cDNA for human NTCP [Hagenbuch et al., J Clin Invest 1994 March; 93(3):1326-1331] was cut with EcoRV and HindI and the coding region ligated into pcDNA5/FRT (Invitrogen, Life-Technologies, Carlsbad, Calif.). CHO FlpIn cells (Invitrogen, Life-Technologies) were transfected with the resulting construct using Lipofectamine® 2000 (Invitrogen, Life-Technologies). Stably transfected cells were selected with 550 μg Hygromycin-B in HAM-F12 medium (Gibco, Invitrogen, Life-Technologies). Transfected cells were cloned with the limiting dilution method. Clones expressing functional NTCP were identified by transport assays with radioactively labeled taurocholate (see below). To further characterize the cloned cells, immunofluorescence localization of NTCP using a polyclonal antibody against NTCP [Kullak-Ublick G et al., Gastroenterology 1997 October; 113 (4):1295-1305] was performed as described by Huber RD et al. [Am J Physiol Cell Physiol 2007 February; 292(2):C795-

C806]. CHO cells expressing OATP1B1, OATP1B3 and OATP2B1 were described previously [Treiber et al., DMD 35:1400-1407, 2007].

Transport Experiments with Stably Transfected Cell Lines

For all transport experiments, cells grown on 3 cm culture dishes were cultured for 24 hours in media supplemented with 5 mmol/L sodium-butyrate to increase expression levels of transfected transporters [Palermo D P et al., J Biotechnol 1991 June; 19(1):35-47].

Transport experiments with uptake of radioactively labeled substrates: These experiments were performed as described by Huber R D et al. [Am J Physiol Cell Physiol 2007 February; 292(2):C795-C806].

Transport experiments with uptake of CLF: Uptake was performed in the same buffers as for the radioactive substrates above. For visualization of CLF uptake, cells were immediately inspected with a Leica-DM-IRBE-inverted-microcope (Leica-Microsystems, Wetzlar, Germany) equipped with a Hamamatsu-ORKA-ER-camera (Hamamatsu-Photonoics, Japan). To determine uptake of CLF, cells were solubilized by the addition of 2 ml 1% (w/v) Triton-X-100. After complete solubilization, 1.5 ml was used to measure fluorescence in a Perkin-Elmer LS-5 luminescence-spectrometer set at $\lambda_{exc}$486 nm (slit 10 nm) and $\lambda_{em}$520 nm (slit 5 nm). Protein was determined with the bicinchoninic acid method using a kit from Interchim (Montfuçon, France). Transport data from OATP expressing cell lines were corrected for binding by subtracting 0 min time points (blank values) and except for FIGS. 2B and 2C were normalized per minute. Kinetic analysis was performed with nonlinear regression of the data to the Michaelis-Menten equation using GraphPad PRISM-V-4.00 (GraphPad-Software-Inc., San Diego, Calif.)

Preparation of Membrane Vesicles

The production of recombinant baculovirus was as described by de Waart et al. [Liver Int 2006 April; 26(3):362-368]. ABCC3 and ABCG2-recombinant baculovirus were a kind gift from Borst [Breedveld P. et al., Cancer Res 2004 Aug. 15; 64(16):5804-5811 and Borst P. et al., J Biol Chem 2001 Dec. 7; 276(49):46400-46407.]. ABCB11-recombinant baculovirus was a kind gift from Thompson [Thompson R J et al., Gastroenterology 2002 November; 123(5):1649-1658]. Sf21 cells grown at 27° C. were infected with ABCB11, ABCC2, ABCC3 and ABCG2-cDNA containing baculovirus. Cells were harvested at 2-4 days after infection. Membrane vesicle preparation was as described by de Waart et al. [Liver Int 2006 April; 26(3):362-368].

Western Blotting and Protein Analysis

Membrane vesicles were fractionated by 6% SDS-PAGE, blotted on nitrocellulose membranes (Schleicher&Schuell, Dassel, Germany) which were blocked in phosphate-buffered saline (PBS)/5% milk powder/0.05% Tween-20. The following antibodies were used: anti-his probe; sc-803 (Santa Cruz, USA), anti-ABCG2; BXP-21 [Maliepaard M et al., Cancer Res 2001 Apr. 15; 61(8):3458-3464], anti-ABCC2; $M_2III6$ [Scheffer et al., Cancer Res 2000 Sep. 15; 60(18):5269-5277] and anti-ABCC3; $M_3III21$ [Scheffer et al., Cancer Res 2000 Sep. 15; 60(18):5269-5277]. Immune complexes were visualized with horseradish-peroxidase-conjugated immunoglobulins and detected using chemiluminescence (Amersham, UK).

Transport Assays with Plasma Membrane Vesicles

Transport studies with membrane vesicles were performed using the rapid filtration technique as described by Heijn M et al. [Am J Physiol 1992 January; 262(1 Pt 1):C104-C110]. Radiolabel was measured with a scintillation counter. When CLF was used as a probe, filters were placed in a glass tube, 0.1% Triton-X-100 was added and the tubes vortexed. Samples were pipetted in 96-well plates (Kartell, Noviglio, Italy) and the amount CLF quantitated by measurement of fluorescence at $\lambda_{exc}$485 nm and $\lambda_{em}$520 nm using a NovoStar (BMG-labtech, Offenburg, Germany).

Animal Experiments

Male mice were housed in a pathogen-free animal facility on a 12 hours light-dark cycle. Mice were anesthetized with a combination of Hypnorm (VetaPharma, UK; 11.8 mg/kg fluanisone and 0.37 mg/kg fentanyl-citrate) and diazepam (Centrafarm, Etten-Leur, The Netherlands; 5.9 mg/kg valium). Body temperature was maintained at 36±1° C. on thermostatted heating pads. For clearance studies, mice were infused with CLF by injecting 100 µL (2 mmol/L) CLF in the tail vein. Subsequently, blood was drawn from the carotis at indicated time points. Blood samples were deproteinised by addition of two volumes methanol and the amount CLF in the supernatant was quantitated by measurement of fluorescence as described above.

For biliary secretion studies, the gall bladder was cannulated with PE10 polyethylene tubing and 100 µL (1 mmol/L) CLF was injected in the tail vein. Bile was collected in 10 minutes fractions; liver and blood were harvested at the end of the experiment. Homogenised livers were deproteinised by adding 2 volumes of MeOH, and bile and blood samples were diluted with 0.1% Triton-X-100. The amount CLF was quantitated by measurement of fluorescence as described above.

For intestinal uptake studies of taurocholate (TC) and CLF, mice were anesthetised and the gall bladder cannulated as described above. Mice received both TC and CLF by injecting 100 µL (2 mmol/L) CLF into the ileum. Bile was collected every 15 minutes. Radioactivity was measured in a scintillation counter and CLF quantitated as described above.

Results

Figure 1B:
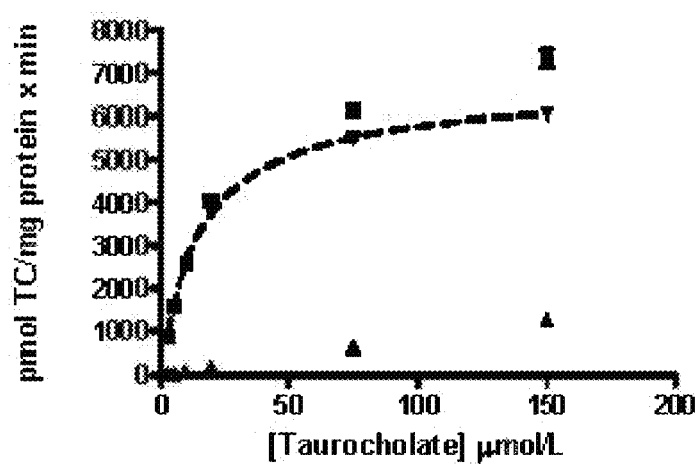
FIG. 1B shows kinetic characterization of CHO-NTCP wherein cells were incubated with increasing TC (taurocholate) concentrations for 45 seconds in the presence of sodium (■) or potassium (▲). Sodium-dependent uptake rates (▼) were used to determine the kinetic parameters. Data represent means±SD of triplicates. Where error bars are absent, they were smaller than the symbol.
Figure 2A:
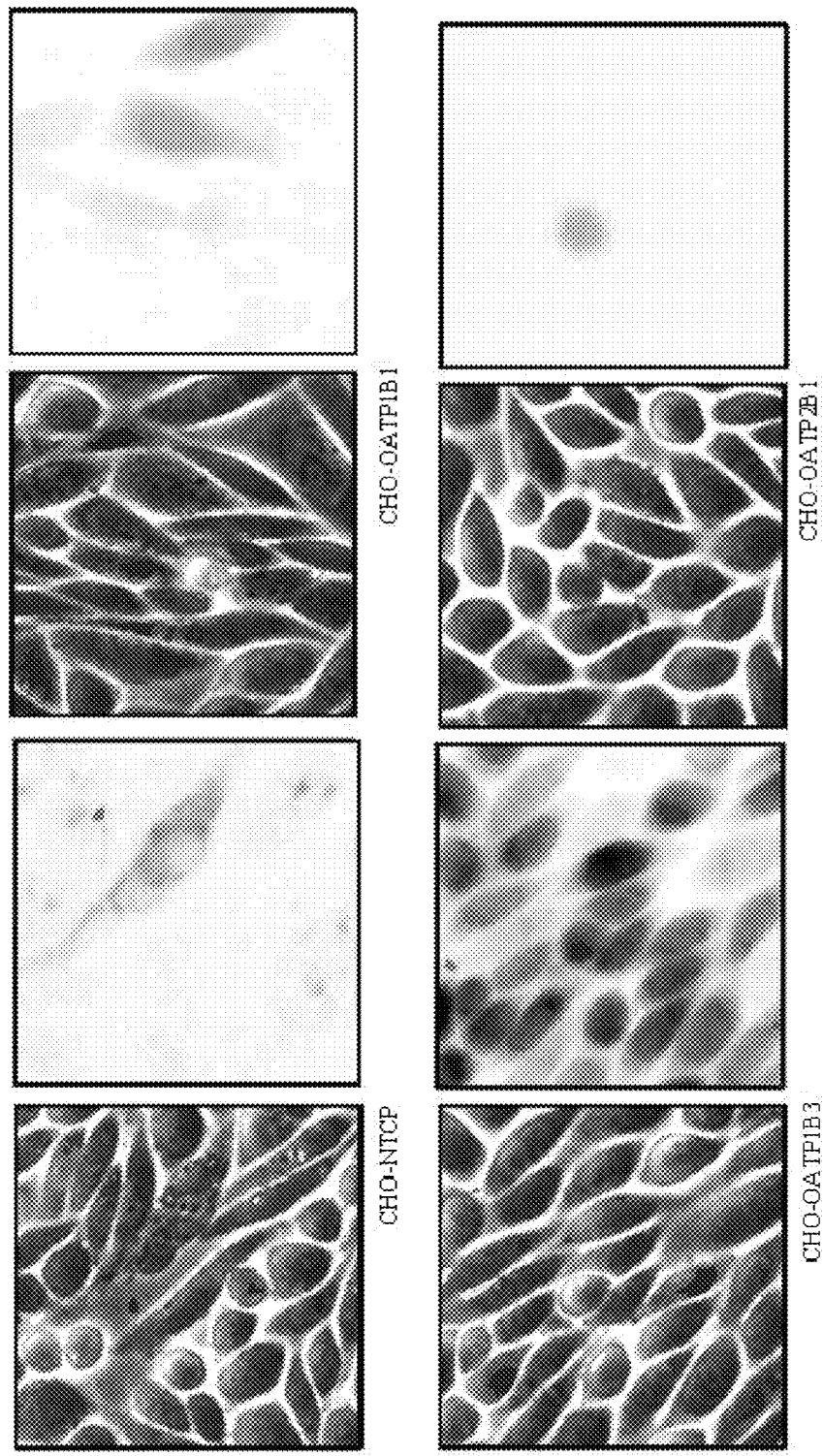
FIGS. 2A-2D relate to uptake studies on CHO cells expressing hepatocellular uptake transporters; the data for FIGS. 2B-2D represent means±SD.
Figure 2B:
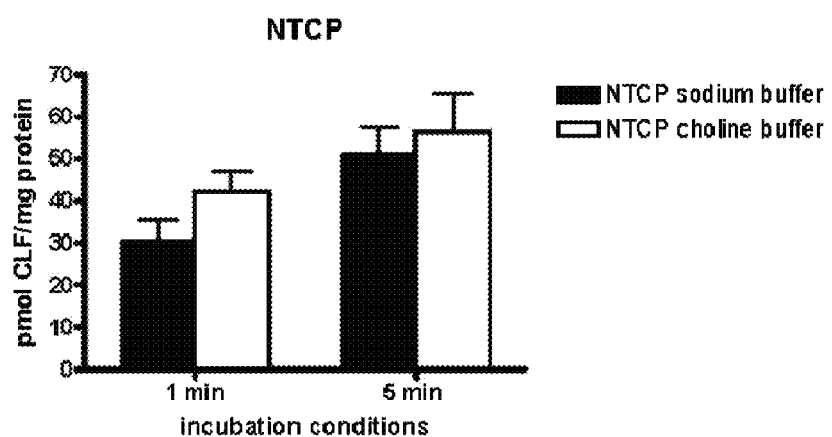

The role of different hepatocellular bile salt transporters in the hepatic uptake of CLF was investigated. For this purpose CHO cells stably expressing NTCP were generated (CHO-NTCP) and characterised. FIG. 1A shows an immunofluorescence micrograph of stably transfected cells from an immunofluorescence assay using a polyclonal antibody against NTCP. An immunofluorescence micrograph for wild type cells (not shown) displayed no fluorescence and therefore no expression of NTCP in wild type CHO cells, but the immunofluorescence micrograph for transfected cells (FIG. 1A) shows fluorescence at the cell membranes and therefore shows clear plasma membrane expression of NTCP in stably transfected cells. Furthermore, uptake of taurocholate (TC) into these cells was sodium dependent (data not shown) and was saturable with increasing taurocholate concentrations. Even at high taurocholate concentrations, uptake in the absence of sodium was negligible (FIG. 1B). The $K_m$ and the $V_{max}$ values were 16.0 µmol/L and 6738 pmol TC/mg protein/min, respectively, for sodium-dependent transport of TC (FIG. 1B). On the contrary, no sodium-dependent uptake of CLF mediated by NTCP could be observed by fluorescence analysis and by quantitative determination of CLF of NTCP cells incubated with CLF (FIGS. 2A and 2B, respectively). The fluorescence picture of the CHO cells expressing NTCP (see FIG. 2A) shows absence of CLF uptake into cells. The long cell towards the right of the picture of CHO cells expressing NTCP, which is exhibiting weak fluorescent staining, may not have been vital anymore. The uptake of CLF in the absence of sodium (FIG. 2B) was comparable to that of wild type cells (not shown) and tended to increase minimally with increasing incubation time.

Figure 2C:
Figure 2D:
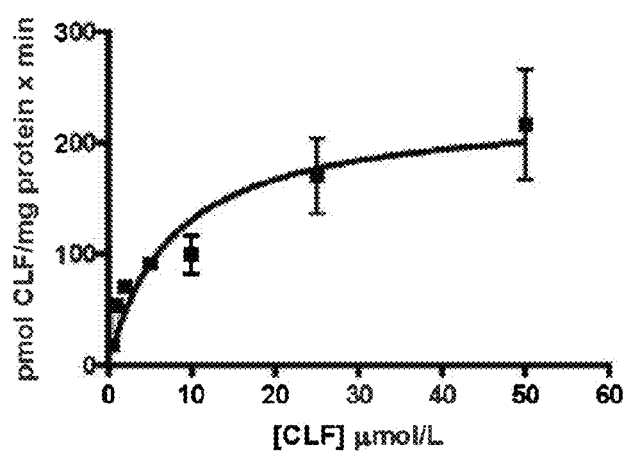

Next, uptake of CLF mediated by OATP1B1, OATP1B3 and OATP2B1 was examined in wild type and stably transfected CHO cells. The fluorescence pictures of the CHO cells expressing OATP1B1, OATP1B3 and OATP2B1 (see FIG. 2A) show uptake of CLF for the CHO cells expressing OATP1B3 but not for OATP1B1 and OATP2B1. The fluorescence picture of the CHO cells expressing OATP1B3 shows strong fluorescent staining of the cells, and therefore shows clear uptake of CLF into the OATP1B3 expressing cells. The fluorescence picture of the CHO cells expressing OATP1B1 shows very weak fluorescent staining, showing that uptake of CLF into OATP1B1 cells was very weak but consistent. In contrast, no uptake into OATP2B1 was found, the fluorescence picture of the CHO cells expressing OATP2B1 showing no fluorescent staining except for a single positive cell visible in the fluorescence picture, which may be a cell with partially reduced vitality, as judged by the phase contrast microscopy. High, time dependent transport rates of CLF were only seen in OATP1B3 expressing CHO cells (FIGS. 2A and 2C, respectively). Uptake of CLF by OATP1B1 cells was consistently observed, but not by OATP2B1 cells (FIGS. 2A and 2C), indicating that CLF is not a substrate for OATP2B1. OATP1B3 mediated CLF transport was concentration-dependent (FIG. 2D) with $K_m$ and the $V_{max}$ values of 4.6±2.7 µmol/L and 213±42 pmol CLF/mg protein/min, respectively (mean of three independent determinations). Uptake experiments with increasing CLF concentrations and OATP1B1 cells showed evidence for saturability (not shown). Due to a low signal to noise ratio, in particular at higher CLF concentrations, no determination of the kinetic parameters was possible.

Figure 3A:
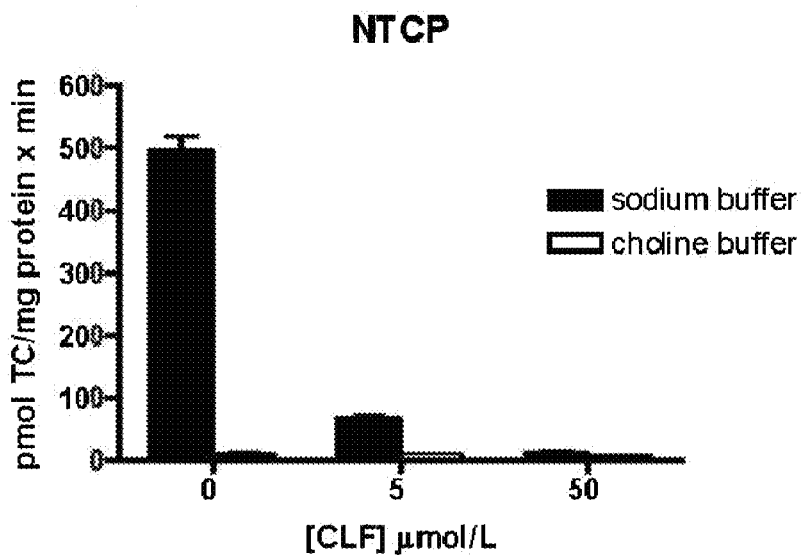
FIGS. 3A-3D relate to inhibition of transport activity of hepatocellular uptake transporters by CLF. CHO cells expressing NTCP, OATP1B1, OATP1B3 and OATP2B1 were incubated with 0, 5 or 50 μmol/L CLF and with the substrates, 2.5 μmol/L TC, 1 μmol/L estrone-3-sulfate, 10 μmol/L TC and 1 μmol/L estrone-3-sulfate, respectively. Data represent means±SD of triplicate determinations.
Figure 3B:
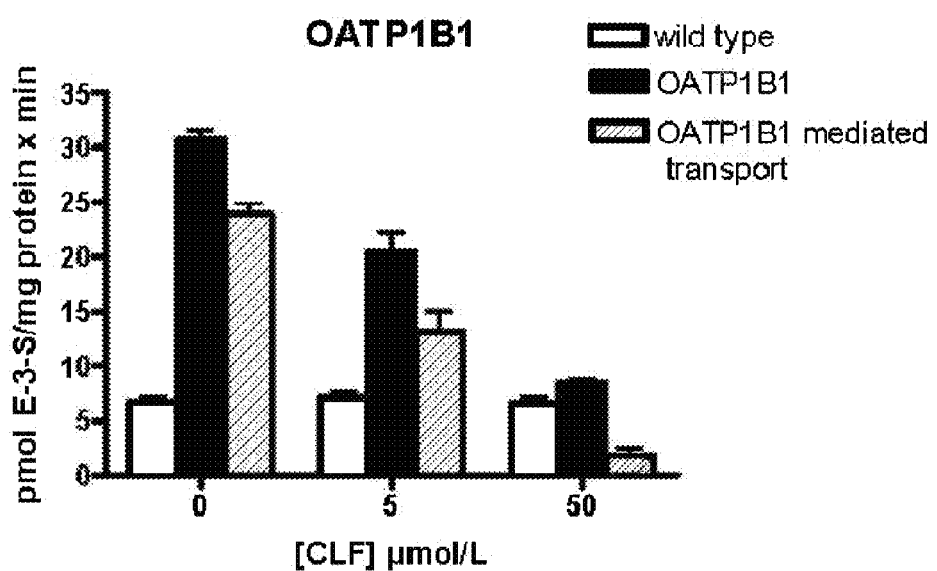
Figure 3C:
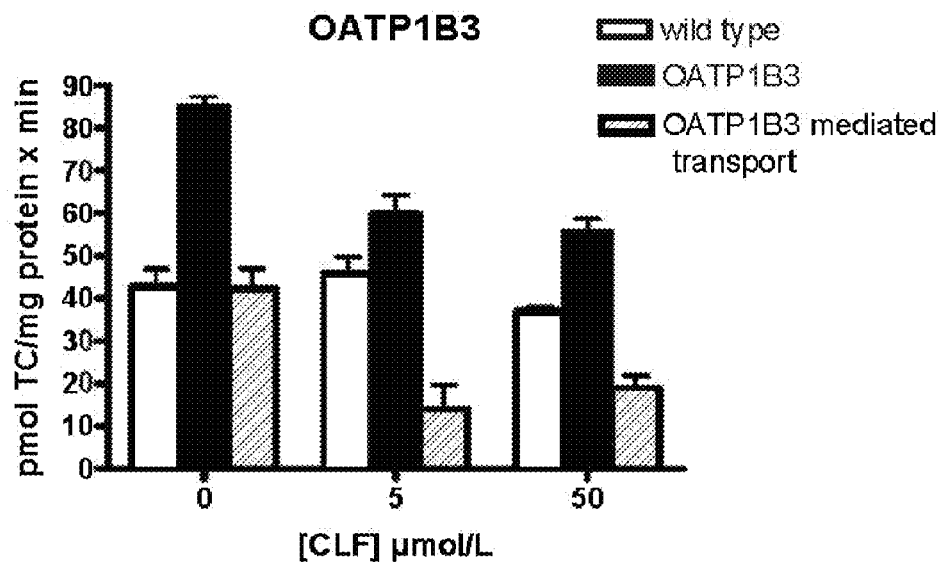
Figure 3D:
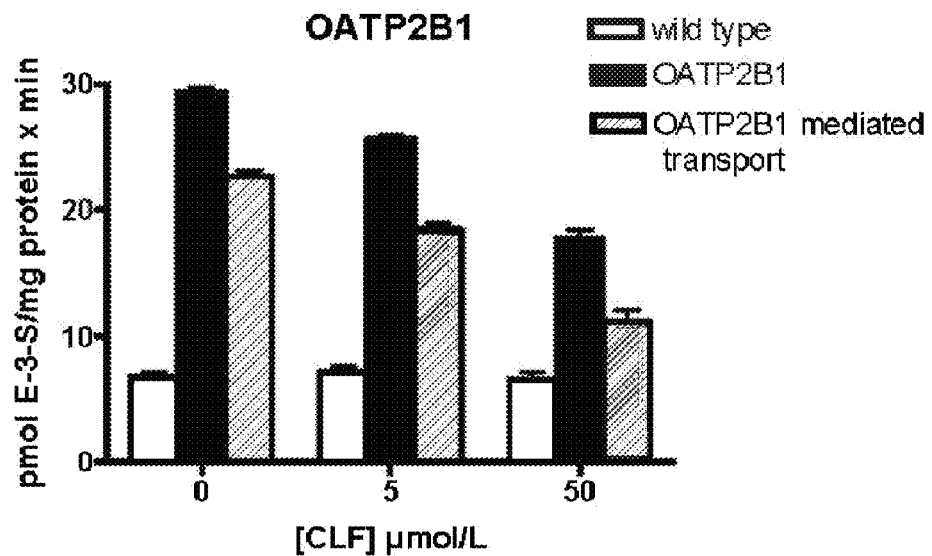

Investigations were carried out to determine whether transport of model compounds mediated by NTCP, OATP1B1, OATP1B3 and OATP2B1 could be inhibited by CLF despite CLF being a substrate for OATP1B3 only. CHO cells expressing NTCP, OATP1B1, OATP1B3 and OATP2B1 were incubated with 0, 5 or 50 µmol/L CLF and with the substrates, 2.5 µmol/L TC, 1 µmol/L estrone-3-sulfate, 10 µmol/L TC and 1 µmol/L estrone-3-sulfate, respectively. Data represent means±SD of triplicate determinations. Strikingly, CLF very efficiently inhibited the transport of TC via NTCP (FIG. 3A). Transport of TC mediated by OATP1B3 could be inhibited by CLF in a dose-dependent manner (FIG. 3C) as expected. Finally, transport of the model substrate estrone-3-sulfate mediated by OATP1B1 and OATP2B1 was inhibited by CLF, albeit much less efficiently (FIGS. 3B and 3D respectively), corroborating the uptake experiments with CLF. Of note, addition of CLF to wild type cells had no influence on substrate uptake indicating that it does not interfere with the structural integrity of the plasma membrane (FIG. 3).

Figure 4A:
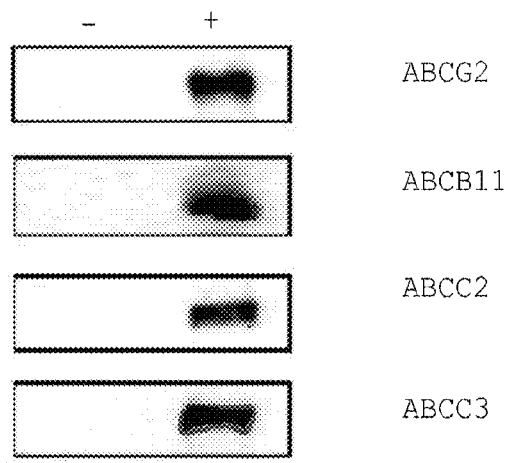
FIG. 4A shows Western blots of membrane vesicles of Sf21 insect cells uninfected and infected with ABCB11, ABCC2, ABCC3 and ABCG2 cDNA containing baculovirus. The Western blots show the presence of proteins ABCB11, ABCC2, ABCC3 and ABCG2 in the respective infected Sf21 insect cells.
Figure 4B:
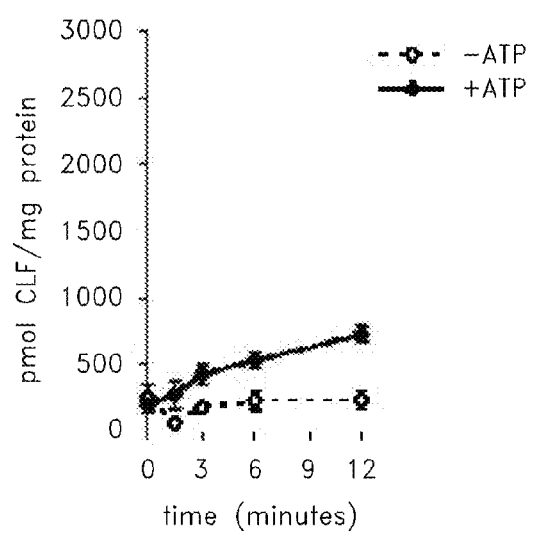
FIGS. 4B to 4F show time-dependent transport of CLF into plasma membrane vesicles from wild type Sf21 cells (B), Sf21 cells expressing ABCB11 (C), ABCG2 (D), ABCC2 (E) or ABCC3 (F), respectively.
Figure 4C:
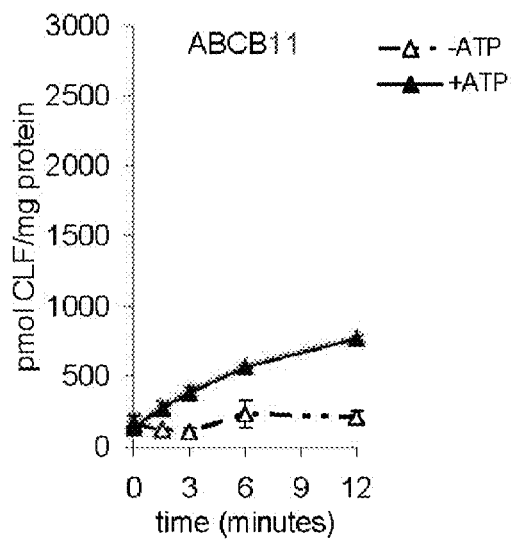
Figure 4D:
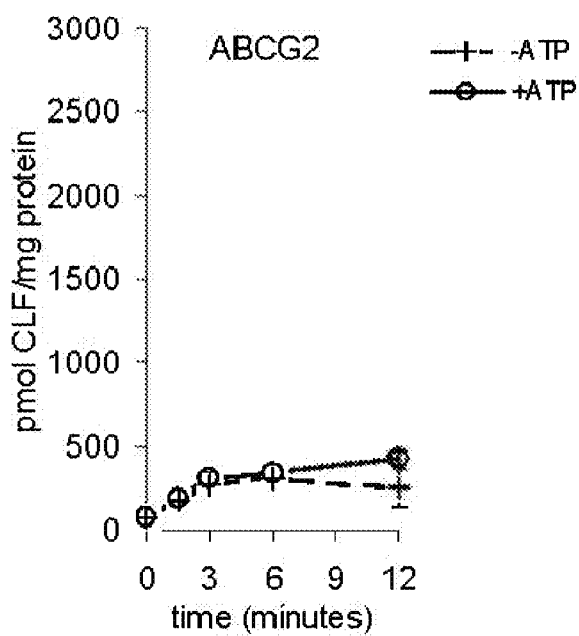
Figure 4E:
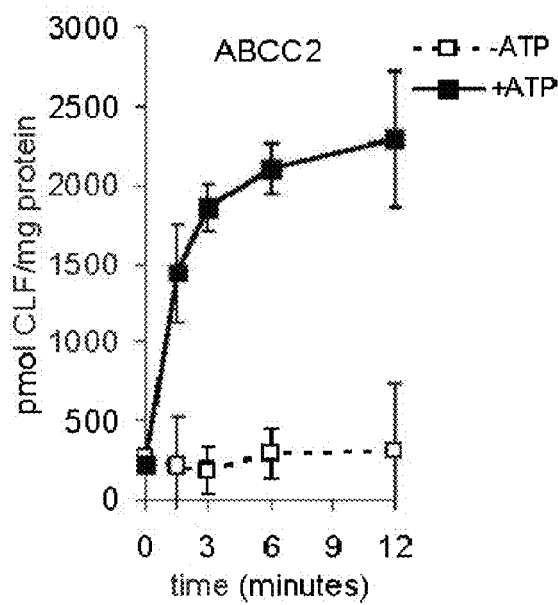
Figure 4F:
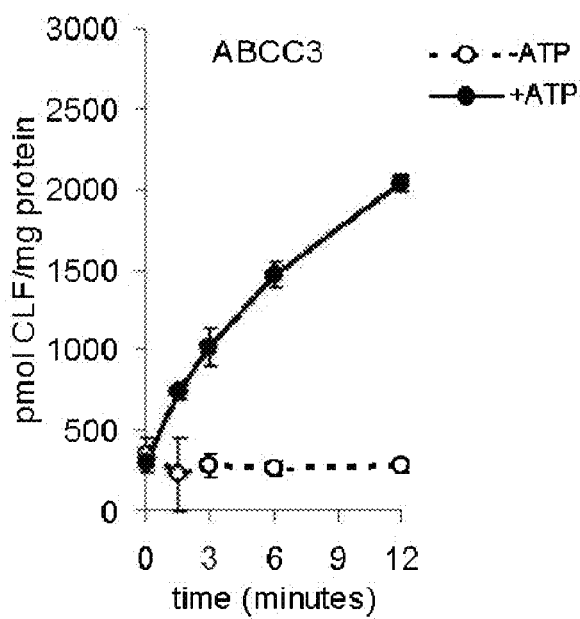

In order to test whether the canalicular ATP-dependent transporters ABCB11, ABCC2 and ABCG2, as well as the basolateral transporter ABCC3, mediate transport of CLF, these human proteins were expressed in Sf21 insect cells (FIG. 4A). FIG. 4B shows that slight ATP-dependent uptake occurred in control vesicles, indicating that an endogenous transporter is able to take up CLF in an ATP-dependent fashion. ATP-dependent transport of CLF in ABCB11 and ABCG2 protein containing membrane vesicles was not higher than in control vesicles (FIGS. 4C and D, respectively). However, ABCC2 and ABCC3 containing membrane vesicles showed much higher CLF transport rates compared to control wild type Sf21 membrane vesicles (FIGS. 4E and F, respectively).

Figure 4G:
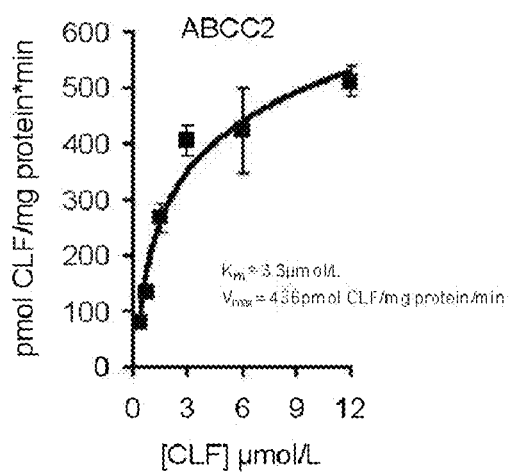
FIGS. 4G and 4H show concentration-dependent uptake of CLF into Sf21 membrane vesicles containing ABCC2 (G) or ABCC3 (H) respectively.
Figure 4H:
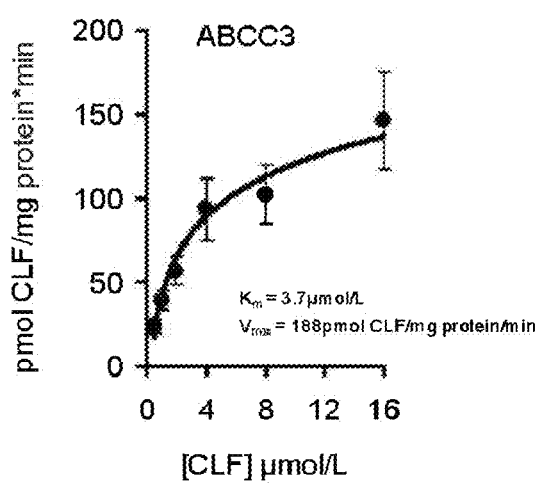

Membrane vesicles (10 µg and 30 µg of total protein for ABCC2 and ABCC3, respectively) were incubated with different concentrations of CLF in the presence or absence of 4 mmol/L ATP. ABCC2 and ABCC3 mediated transport of CLF was concentration-dependent (FIGS. 4G and H, respectively). The $K_m$ values were 3.3±2.0 µmol/L and 3.7±1.0 µmol/L for ABCC2 and ABCC3, respectively, and $V_{max}$ values were 436±215 pmol CLF/mg protein/min and 188±55 pmol CLF/mg protein/min, respectively.

Figure 5A:
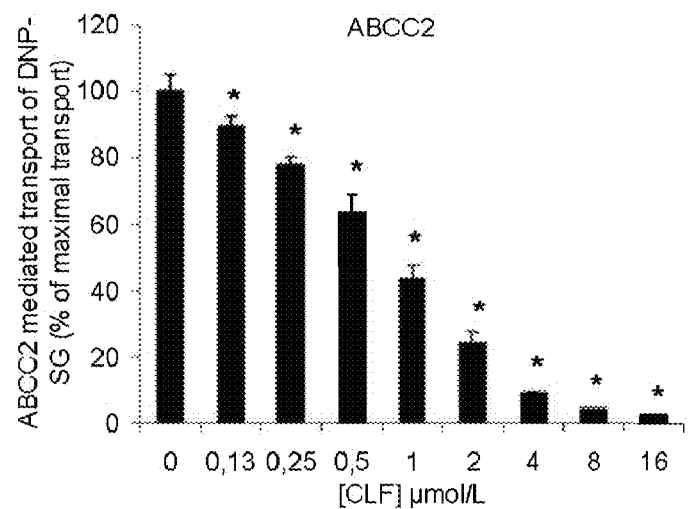
FIGS. 5A and 5B show CLF inhibition of DNP-SG and TC transport into ABCC2 (A) and ABCB11 (B) protein containing Sf21 membrane vesicles respectively. The values are expressed as a percentage of maximal ATP-dependent transport. Significance was tested using two-sided Student's t-test: *$P<0.05$ for transport in the presence vs. absence of inhibitor.
Figure 5B:
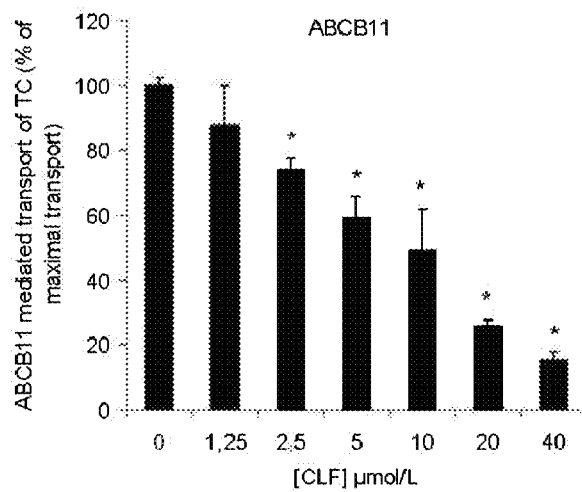

Another model substrate for ABCC2 is dinitrophenyl-glutathione (DNP-SG) and CLF should inhibit transport of this compound. Half maximal inhibition of DNP-SG transport with CLF was achieved at approximately 1 µmol/L (FIG. 5A). Although no indication was found that CLF is a substrate for ABCB11, it contains the cholyl moiety and therefore, it might be able to inhibit bile salt transport via ABCB11. Indeed, TC transport could be inhibited by CLF in a dose dependent fashion and the concentration at which half maximal transport was observed was approximately 10 µmol/L (FIG. 5B).

Figure 6:
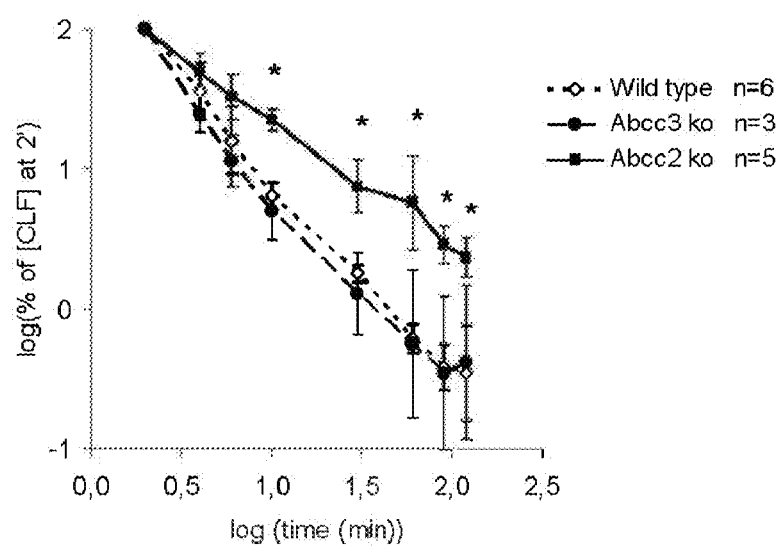
FIG. 6 shows plasma clearance of CLF in mice. Wild type, Abcc3$^{-/-}$ and Abcc2$^{-/-}$ mice received 100 μL of 2 mmol/L CLF by injection in the tail vein. After the indicated time points blood was drawn. Data are expressed as the mean percentage of the initial CLF level at 2 minutes. Significance was tested using two-sided Student's t-test: *$P<0.05$ for Abcc2−/− vs wild type mice.
Figure 7A:
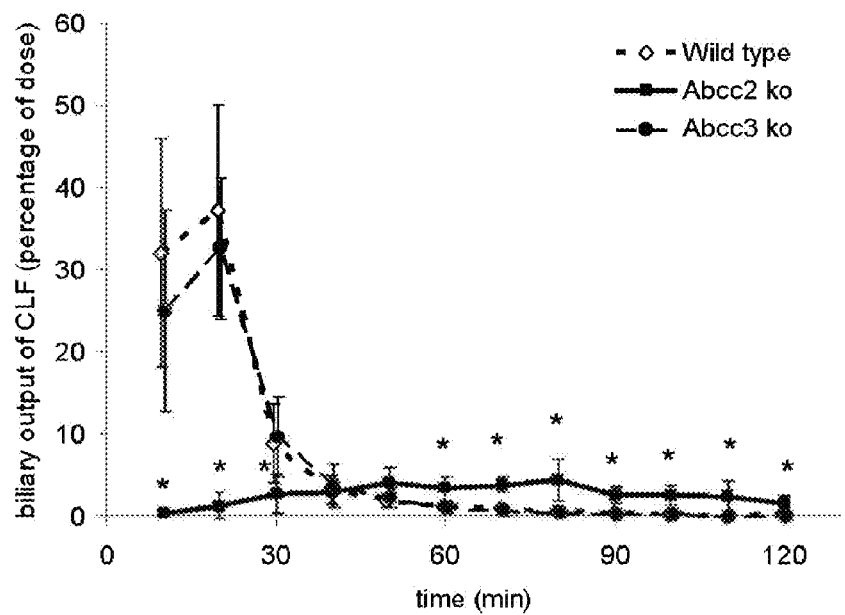
FIG. 7A shows time dependent appearance of CLF in bile of wild type, Abcc3$^{-/-}$ and Abcc2$^{-/-}$ mice. Data represent means±SD.
Figure 7B:
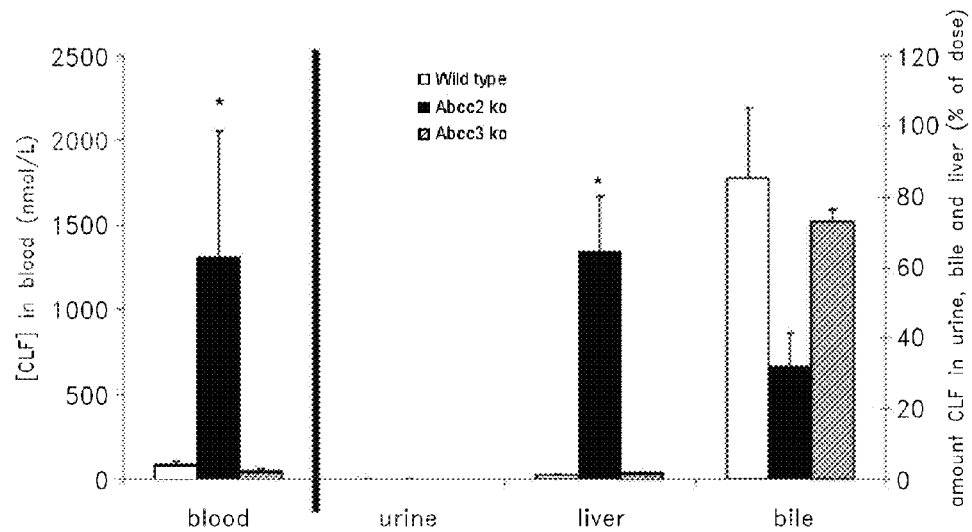
FIG. 7B shows CLF levels in blood, urine, liver and bile of wild type, Abcc3$^{-/-}$ and Abcc2$^{-/-}$ mice after 2 hours. Mice received 100 μL of 1 mmol/L CLF by injection in the tail vein. Data represent means±SD. Plasma levels are expressed in nmol/L and levels in urine, liver and bile as percentage of administered dose. Significance was tested using two-sided Student's t-test: *$P<0.05$ for Abcc2$^{-/-}$ vs wild type mice. Data represent means±SD.
Figure 8:
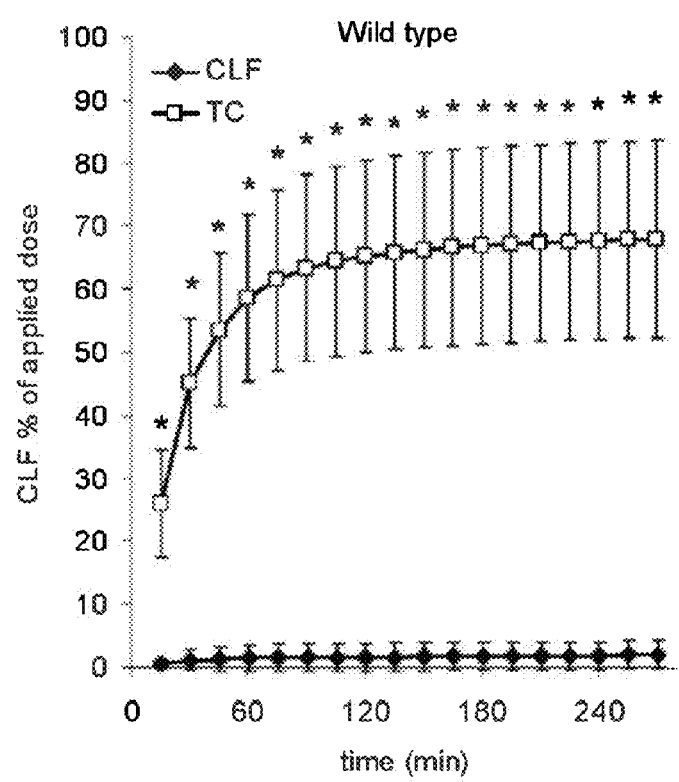
FIG. 8 relates to intestinal uptake of TC and CLF. Appearance of TC and CLF in bile after ileal administration of 100 μL mixture of 2 mmol/L TC and CLF in wild type mice. Bile was collected after indicated time points. Data represents means±SD. The graph is a plot of cumulative biliary levels as percentage of applied dose. Significance was tested using two-sided Student's t-test: *$P<0.05$ for TC uptake vs CLF uptake.

To investigate the role of Abcc2 and Abcc3 in plasma clearance of CLF, CLF levels in plasma of wild type, Abcc2$^{-/-}$ and Abcc3$^{-/-}$ mice after a single injection of CLF in the tail vein were examined. Clearance of CLF was strongly impaired in Abcc2$^{-/-}$ mice in comparison with wild type mice but not affected in Abcc3$^{-/-}$ mice (FIG. 6). To examine the role of Abcc2 in biliary output of CLF, infusion experiments were performed with wild type and Abcc2 deficient mice. Biliary excretion of CLF was very much delayed in the Abcc2$^{-/-}$ mice (FIG. 7A). As a consequence, almost 70% of the CLF dose was excreted into bile in wild type mice within 20 minutes, whereas in the same time span less than 2% was excreted into bile in Abcc2$^{-/-}$ mice. At 120 minutes after administration (FIG. 7B), the cumulative biliary excretion of CLF was still significantly higher in wild type mice than in Abcc2$^{-/-}$ mice (85% vs 32% of the administered dose) which resulted in a significantly higher hepatic retention of CLF in Abcc2$^{-/-}$ vs wt mice (64% vs 1% of the administered dose) and in higher blood levels in Abcc2$^{-/-}$ vs wt mice (1306±749 nmol/L vs 83±21 nmol/L). These data indicate that, in mice, Abcc2 is the main transporter responsible for the biliary excretion of CLF. In line with the observations from FIG. 7A, it was observed that biliary output of CLF was not affected in Abcc3$^{-/-}$ mice in comparison with wild type mice and no differences in plasma and liver CLF contents were found (FIG. 7B).

After excretion into bile and delivery into the duodenum, bile salts are taken up in the ileum via the apical sodium dependent bile acid transporter (ASBT) [Wong M H et al., J Biol Chem 1995 Nov. 10; 270(45):27228-27234]. To investigate whether CLF is taken up in the intestine, equimolar amounts of CLF and [$^3$H]TC were injected into duodenum or ileum of wild type FVB mice. Thereafter, bile was collected and the amounts of [$^3$H]TC and CLF excreted in bile were quantified. At 4.5 hours after ileal injection of both compounds, only 2% of the CLF was recovered in bile whereas this was 68% for [$^3$H]TC. Hence, uptake of CLF in the terminal ileum is minimal. This shows that CLF is not a good substrate for the Asbt.

Conclusions

The results of the investigations into uptake of CLF show that uptake of CLF into hepatocytes is not likely to be mediated by NTCP, since no uptake of CLF into CHO cells expressing human NTCP was found. This was not due to a non-functional protein, since these cells were fully capable of mediating the uptake of the natural occurring bile salt, TC. The ileal counterpart of hepatic NTCP is ASBT and it mediates transport of conjugated and unconjugated bile salts [Geyer J et al., Arch Pharmacol 2006 March; 372(6):413-431]. Indirect evidence has been obtained to suggest that CLF is not transported via (murine) Asbt, whereas TC injected in the ileal lumen of wild type mice was very efficiently recovered in bile (almost no CLF was found). These data suggest that both NTCP and Asbt, which are homologous sodium-dependent bile salt transporters, are unable to transport CLF.

Previous studies showed partial sodium-dependent uptake of some, but not all, fluorescent bile salts into rat hepatocytes [Maglova L M et al., Hepatology 1995 August; 22(2):637-647]. In addition, uptake of cholyl-glycyl-fluorescein into CHO cells expressing rat Ntcp, but not wild type cells, has been demonstrated [Boyer J L et al., Am J Physiol 1994 March; 266(3 Pt 1):G382-G387]. In contrast to CLF, another bile salt conjugate, taurocholyl-chlorambucil, was found to be a substrate for NTCP [Kullak-Ublick G A et al., Gastroenterology 1997 October; 113(4):1295-1305]. The latter compound is a conjugate at the 3-OH group of the bile salt whereas CLF is conjugated at the side chain. In this context it is interesting that Baringhaus et al. determined the pharmacophore of both NTCP and ASBT and found that the 3-OH group is not essential for transport whereas the acidic side chain is [Baringhaus K H et al., J Lipid Res 1999 December; 40(12):2158-2168]. The above data is completely in line with this model and indicate a species difference of the substrate specificity of NTCP/Ntcp.

The less specific bile salt transporter, OATP1B3, turns out to be a more likely candidate for uptake into the hepatocyte, which fits with the broad substrate specificity of this transporter [Hagenbuch B et al., Pflugers Arch 2004 February; 447(5):653-665].

These data demonstrate, surprisingly but conclusively, that ABCC2/Abcc2 is the most prominent transporter responsible for biliary excretion of CLF and not ABCB11. In mice, the large majority of CLF in plasma is excreted into bile via Abcc2. It may be argued that the substrate specificity of human ABCC2 can be different from that in mice. However, in plasma membrane vesicle assays it is demonstrated that transport of CLF via human ABCB11 is insignificant compared to that via human ABCC2. Our present data show decisively that CLF is not transported via ABCB11.

As described above, Mills et al. used Abcc2 deficient, TR⁻ rats and measured CLF in bile after injection of CLF in the jugular vein [J Hepatol 1999 October; 31(4):678-684]. The cumulative amount of CLF in bile was similar in TR⁻ and normal Wistar rats after 30 minutes. However, based on these new data, it seems the cumulative data was misinterpreted (namely initial transport rates could still be different). The new tests, described herein, performed a similar but more extensive study using wild type and Abcc2$^{-/-}$ mice. In mice deficient in Abcc2, biliary excretion of CLF was strongly impaired and retained in the liver, which suggests that Abcc2 and not Abcb11 is the major transporter responsible for biliary excretion of CLF. As there is still residual biliary transport of CLF in Abcc2$^{-/-}$ mice, a contribution of Abcb11, albeit small, cannot be excluded.

Loss of MRP2 function is often well tolerated and compensated by the upregulation of other membrane transporters, particularly MRP3 [Nies et Al. Pflugers Arch (2007) 453:643-659]. The investigations show that not only ABCC2, but also ABCC3 mediates the transport of CLF. Therefore if MRP2 is downregulated in patients, this may be compensated by upregulation of MRP3, and the functional activity of the MRP2 and/or MRP3 pathway of the subject can be investigated using CLF.

EXAMPLE 2

A study was carried out in twelve healthy volunteers (six males, six females) aged 21-40 years to compare the plasma pharmacokinetics of CLF after a single 15 second intravenous injection of 2 mg CLF, in the presence of medication-induced changes in biliary transporter proteins. The study was carried out under conditions of no pre-treatment, pre-treatment with rifampicin, also known as rifampin (a non-specific inducer and inhibitor of hepatic clearance pathways), and pre-treatment with cyclosporine (cyclosporine is a known inhibitor of MRP2 [Jedlitschky et al., Expert Opin Drug Metab Toxicol 2006 Jun. 2(3):351-66]).

CLF was obtained from Norgine, Harefield, United Kingdom. Subjects were studied supine. 2 mg CLF was administered on three occasions by 15 second intravenous injection on the morning of day D01 after an overnight fast and rest with the following modalities:

Treatment R: no pre- or co-medication
Treatment T1: ambulatory visits on the evening of Day D-7 until the evening of Day-2 for a single evening dose of 600 mg rifampicin; the last dose of rifampicin was administered on the evening of Day D-1 after admission
Treatment T2: single dose of 100 mg cyclosporine on the evening of D-1 and on the morning of D01 one hour before administration of CLF.

Venous blood samples were collected before injection and 2, 5, 10, 15, 20, 30, 45, 60, 75, 90, 105, 120, 150, 180, 240 and 360 minutes after dosing (17 samples). The level of CLF in each sample was determined using HPLC.

Figure 9:
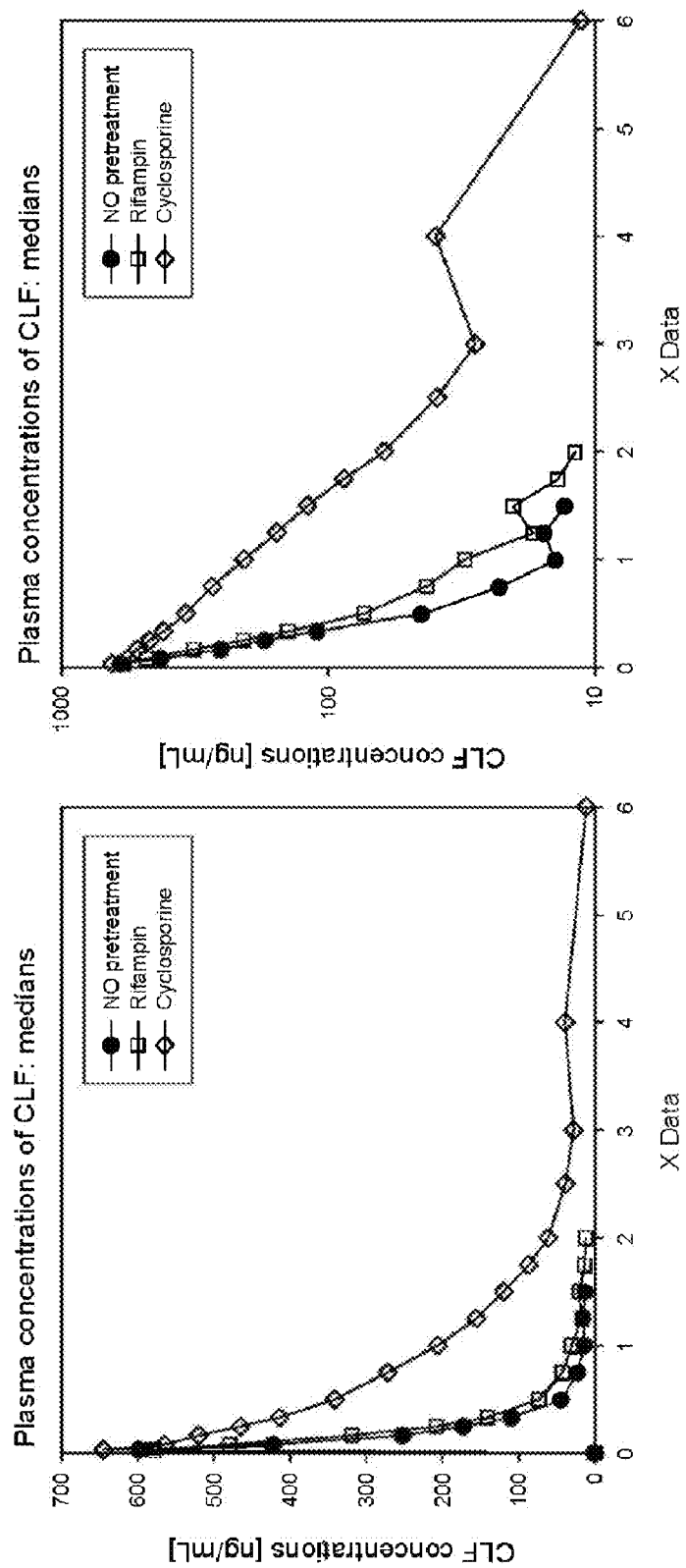
FIG. 9 shows plasma elimination curves relating to Example 2. The left hand graph has a linear and the right hand graph has a log-linear axis.

The time course of the observed median plasma CLF concentrations are presented in FIG. 9. It can be seen that pre-treatment with rifampicin resulted in a slight reduction of the elimination and clearance of CLF. Pre- and co-treatment with cyclosporine caused a distinct inhibition of the elimination and clearance of CLF. This study shows that CLF can be used to determine the OATP1B3 activity and/or MRP2/3 activity of a subject wherein the subject has been pre-treated with drug substrates that affect OATP1B3 activity and/or MRP2/3 activity.

EXAMPLE 3

A study was carried out in twelve healthy volunteers (six males, six females) aged 21-40 years to compare the plasma pharmacokinetics of CLF after a single 15 second intravenous injection of 2 mg CLF in the presence of medication-induced changes in biliary transporter proteins. Interaction with ursodeoxycholic acid and cloxacillin was studied in this example.

CLF was obtained from Norgine, Harefield, United Kingdom. Subjects were studied supine. 2 mg CLF was administered on three occasions by 15 second intravenous injection on the morning of day D01 after an overnight fast and rest with the following modalities:

Reference R: no pre-treatment
Treatment T1: pre-treatment and co-treatment with 1 g cloxacillin t.i.d for three days from the morning of D-3 until the morning of Day D01 0:30 h before administration of CLF
Treatment T2: three week pre-treatment with daily doses of 500 mg b.i.d ursodeoxycholic acid (in the morning and in the evening each time with food) until the evening of Day D-1

Venous blood samples were collected before injection and 2, 5, 10, 15, 20, 30, 45, 60, 75, 90, 105, 120, 150, 180, 240 and 360 minutes after dosing (17 samples). The level of CLF in each sample was determined using HPLC.

Figure 10:
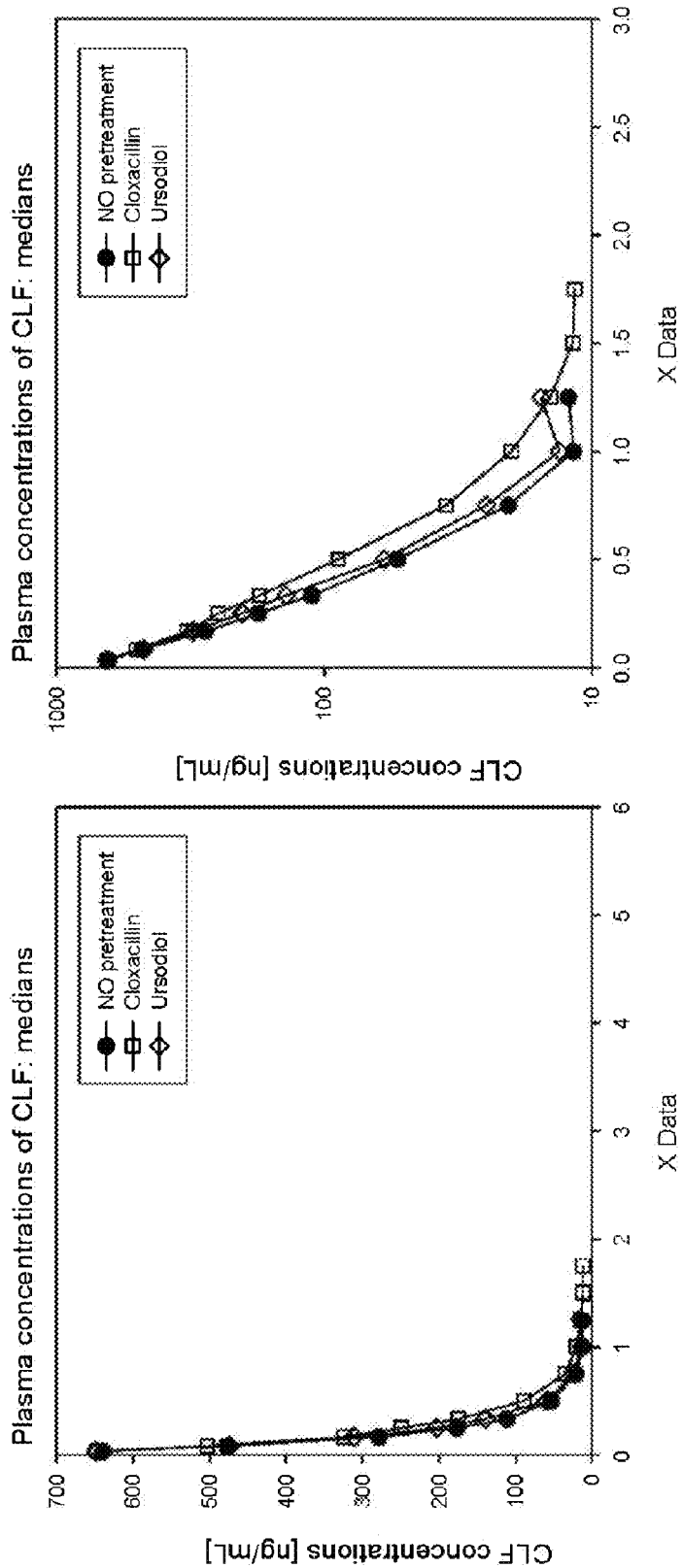
FIG. 10 shows plasma elimination curves relating to Example 10. The left hand graph has a linear and the right hand graph has a log-linear axis.

The time course of the observed median plasma CLF concentrations are presented in FIG. 10. It can be seen that pre- and co-treatment with cloxacillin (a known BSEP inhibitor)

shows a slight, but statistically significant inhibition of the elimination and clearance of CLF. In contrast, a pre-treatment with ursodeoxycholic-acid had no effect (ursodiol is a known multi-factorial enhancer and facilitator of hepatic biliary clearance).

These examples show that CLF can be used to determine medication induced changes in MRP2/3 activity of a subject.

What is claimed is:

1. A method of determining the functional activity of the MRP2 efflux pathway of a human or animal subject, said method comprising:
   (i) determining a level of a bile acid derivative wherein the bile acid derivative is a cholyl-lysyl-fluorescein having the formula:

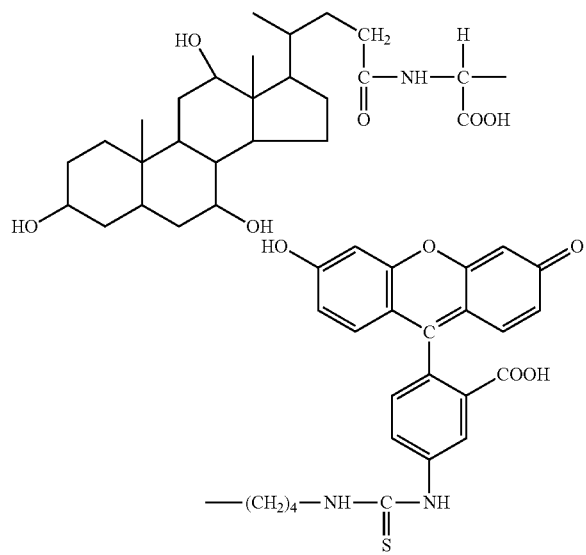

or salt thereof, in the blood of said human or animal subject at two or more predetermined time intervals after introducing an amount of the bile acid derivative into the subject; and
   (ii) using the level of bile acid derivative obtained in step (i) to arrive at a numerical value, wherein the numerical value indicates the functional activity of the MRP2 efflux pathway of the subject, wherein the determination obtained at a first time interval after administration and the determination obtained at a second time interval after administration are expressed as a ratio or percentage.

2. A method according to claim 1, wherein the level of bile acid derivative at 30 or 60 minutes after administration is expressed as a ratio to the level of bile acid derivative at 10 minutes after administration.

3. A method according to claim 1, wherein the level of bile acid derivative at 30 minutes after administration is expressed as a ratio to the level of bile acid derivative at 10 minutes after administration.

4. A method according to claim 1, wherein the level of bile acid derivative at 30, 60 or 90 minutes after administration is expressed as a percentage of the level of bile acid derivative at 10 minutes after administration.

5. A method according to claim 1, wherein the level of bile acid derivative at 30 minutes after administration is expressed as a percentage of the level of bile acid derivative at 10 minutes after administration.

6. The method according to claim 1, further comprising the step of providing at least one sample of blood which has passed through the liver of the subject and which sample has been collected at a time interval after administering the bile acid derivative to the subject, wherein the at least one blood sample is processed to obtain blood plasma or blood serum.

7. The method according to claim 6, wherein the at least one blood sample is processed by centrifugation.

8. The method according to claim 6, wherein blood proteins are separated from the blood plasma or blood serum.

9. The method according to claim 1, wherein the bile acid derivative is administered to the subject intravenously.

* * * * *